United States Patent [19]

Ohnuma et al.

[11] Patent Number: 5,066,645

[45] Date of Patent: Nov. 19, 1991

[54] EPIPODOPHYLLOTOXIN ALTROSIDE DERIVATIVES

[75] Inventors: Takeshi Ohnuma, Tokyo; Hideaki Hoshi, Ichikawa; Hideo Kamei, Tokyo; Takayuki Naito, Kawasaki, all of Japan

[73] Assignee: Bristol-Myers Company, New York, N.Y.

[21] Appl. No.: 401,712

[22] Filed: Sep. 1, 1989

[51] Int. Cl.$^5$ .................... A61K 31/70; C07H 15/20; C07H 15/26
[52] U.S. Cl. ........................... 514/27; 514/33; 514/35; 536/4.1; 536/17.1; 536/18.1; 536/17.2; 536/18.4
[58] Field of Search ............... 536/17.1, 18.1, 17.2, 536/18.4, 4.1; 514/33, 27, 35

[56] References Cited

U.S. PATENT DOCUMENTS

| | | | |
|---|---|---|---|
| 3,524,844 | 8/1970 | Keller-Juslen et al. | 536/18.1 |
| 4,547,567 | 10/1985 | Umezawa et al. | 536/17.2 |
| 4,564,675 | 1/1986 | Kurabayashi et al. | 536/18.1 |
| 4,716,221 | 12/1987 | Umezawa et al. | 536/17.2 |

FOREIGN PATENT DOCUMENTS

| | | |
|---|---|---|
| 956939 | 10/1974 | Canada . |
| 162701 | 11/1985 | European Pat. Off. . |
| 226202 | 6/1987 | European Pat. Off. . |
| 219196 | 12/1983 | Japan . |
| 225096 | 12/1983 | Japan . |
| 192793 | 8/1988 | Japan . |

OTHER PUBLICATIONS

C. Keller-Juslen, et al., "J. Med. Chem.", 1971 (10) 936-940, *Synthesis and Antimitotic Activity of Glycosidic Lignan Derivatives Related to Podophyllotoxin*[1].

H. Saito et al., "Chem. Lett.", 1987, 799-802, *Syntheses of All Four Possible Diastereomers of Etoposide and Its Aminoglycosidic Analogues via Optical Resolution of (+)-Podophyllotoxin by Glycosidation with D- and L-Sugars*.

K. Yamashita, et al., "J. Pharm. Biomed. Anal.", 1987, 5(1):11-20, *Measurement of Plasma Etoposide by Radioimmunoassay*.

*Primary Examiner*—Johnnie R. Brown
*Assistant Examiner*—Nancy S. Carson
*Attorney, Agent, or Firm*—Mollie M. Yang

[57] ABSTRACT

The present invention provides antitumor 4'-Demethylepipodophyllotoxin glycosides characterized by the fact that the glycoside moiety is altrose.

21 Claims, 6 Drawing Sheets

EPIPODOPHYLLOTOXIN ALTROSIDE DERIVATIVES

BACKGROUND OF THE INVENTION

1. Field of the Invention

The present invention relates to 4'-demethylepipodophyllotoxin glycosides, to their use as antitumor agents, and to pharmaceutical compositions containing them.

2. Background Art

4'-Demethylepipodophyllotoxin glucosides of Formula I are antitumor agents derived from the naturally occurring lignin, podophyllotoxin II.

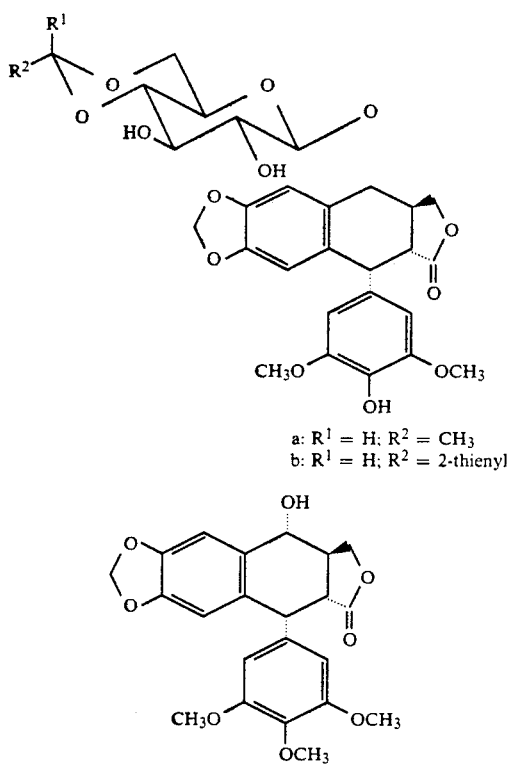

a: $R^1 = H$; $R^2 = CH_3$
b: $R^1 = H$; $R^2 = 2$-thienyl

The method for their synthesis is described in U.S. Pat. No. 3,524,844 to Keller-Juslen et al. Among compounds of Formula I, etoposide (Ia) and teniposide (Ib) have been established as clinically useful against a variety of tumors including small cell lung, ovarian, testicular, breast, bladder, brain, non-lymphocytic leukemia, and Hodgkin's disease.

A number of homologs, analogs and derivatives of etoposide and teniposide have been prepared and studied for antitumor activity. With few exceptions, they have been characterized by the presence of a D-glucose moiety.

Three D-galactopyranosides were reported in J. Med. Chem., 1971 (10) 936–40 and several L-glucopyranosides have been described in Chem. Lett., 1987, 799–802.

Analogs of etoposide in which one of the sugar hydroxyl groups is replaced by an amino or alkylamino group are disclosed in U.S. Pat. Nos. 4,547,567 and 4,716,221.

4'-Phosphate etoposide, a water-soluble prodrug of etoposide, is disclosed in Japan Kokai 63-192793.

Copending and commonly assigned U.S. patent application Ser. No. 240,971 describes and claims epipodophyllotoxin glucosides in which one or both of the sugar hydroxyl groups are replaced by fluorine.

4'-Demethylepipodophyllotoxin glucosides wherein the hydroxyl groups of the glucose moiety are acylated and the phenolic group is protected have been reported as intermediates for the preparation of the corresponding 4'-demethyl-epipodophyllotoxins such as compounds of Formula I.

Canadian Patent No. 956,939 discloses compounds of Formula (III)

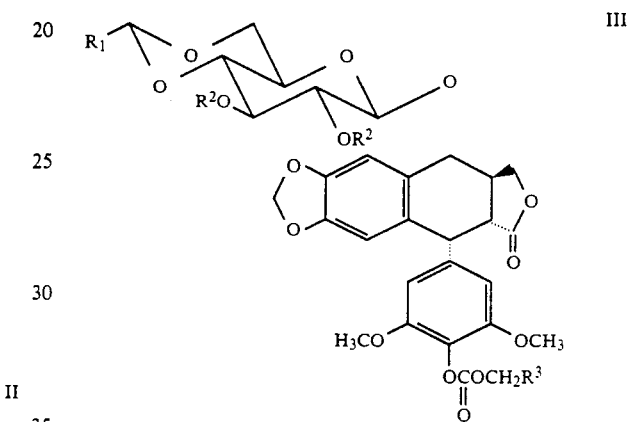

wherein $R^1$ is $C_{1-5}$ alkyl; $R^2$ is acetyl or formyl; and $R^3$ is phenyl or substituted phenyl; possible substituted phenyls mentioned but not exemplified are p-nitrophenyl and p-methoxyphenyl.

U.S. Pat. No. 4,564,675 discloses compounds of the Formula (IV)

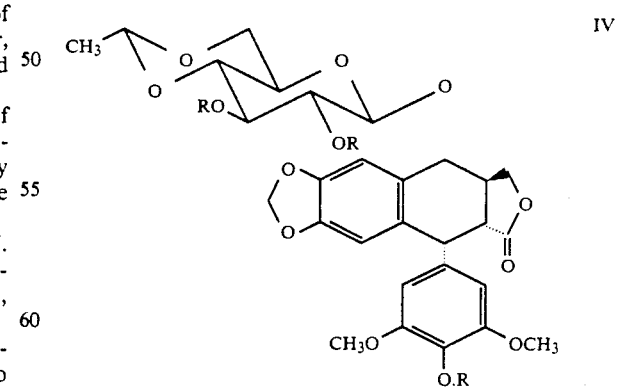

wherein R is —C(O)CH$_2$X, X is a halogen atom.

European Patent Application 162,701 discloses compounds of Formula (V)

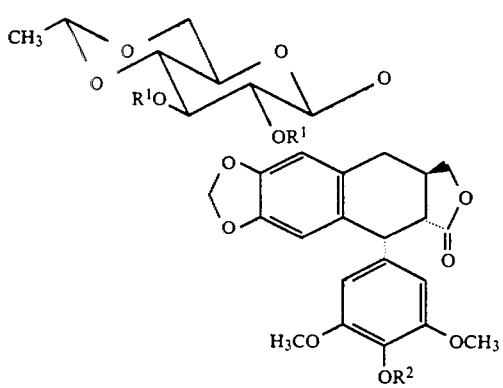

V

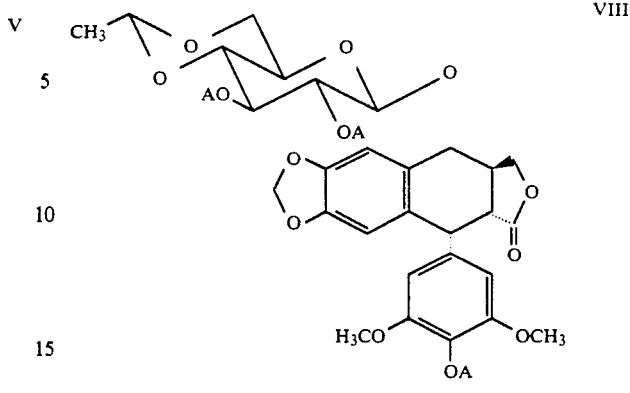

VIII wherein A represents an acetyl group.

Mono-hemisuccinate derivatives of etoposide having the Formula IX are reported in J. Pharm. Biomed. Anal., 1987, 5(1): 11–20 wherein $R^1$ and $R^2$ may be the same or different and each represents $-C(O)CHX_2$ or $-C(O)CX_3$ wherein X is a halogen atom.

Japan Kokai 58-225,096 (Derwent Abst. No. 84-0324268/06) and 58-219,196 (Derwent Abst. No. 84-027495/05) disclose compounds of Formulas (VI) and (VII), respectively.

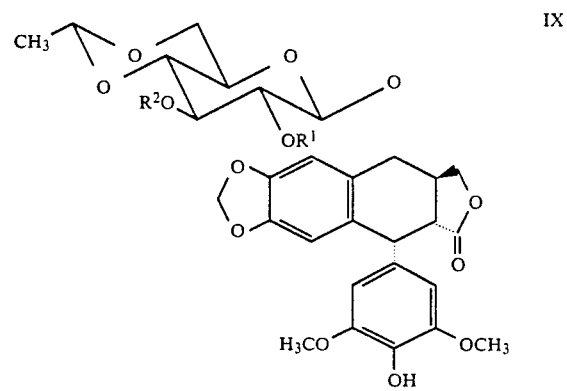

IX

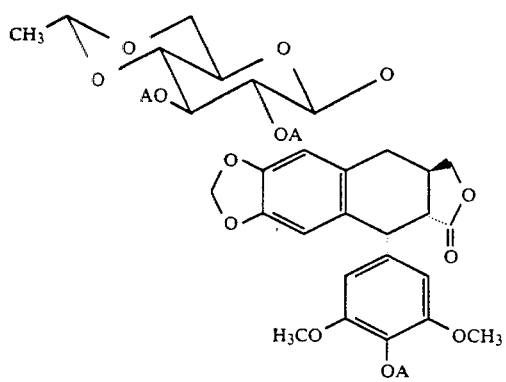

VI wherein one of $R^1$ and $R^2$ is H and the other is $-CO(CH_2)_2CO_2H$. These compounds are used as a means to conjugate etoposide to bovine serum albumin.

SUMMARY OF THE INVENTION

The present invention provides antitumor compounds of Formula X

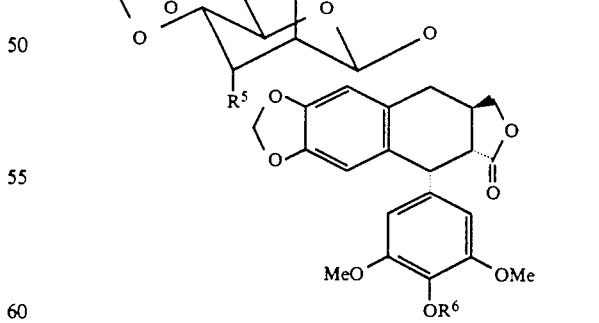

X

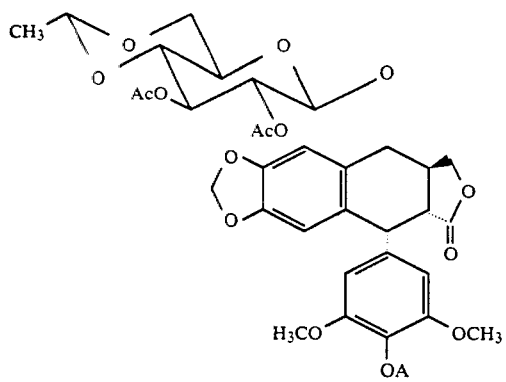

VII wherein A stands for $-CO_2-CH_2-C(H)_m(X)_n$ wherein X is a halogen atom and m is 0 to 2 and n is 1 to 3, m+n=3 and Ac is acyl.

European Patent Application 226,202 discloses an intermediate for etoposide synthesis having the Formula (VIII)

wherein $R^3$ is selected from the group consisting of ($C_1$-$C_{10}$) alkyl, phenyl, furyl and 2-thienyl; wherein one of $R^4$ and $R^5$ is selected from the group consisting of hydroxy, $C_{1-5}$alkoxy and $C_{1-5}$acyloxy; and the other is selected from the group consisting of H, hydroxy, $C_{1-5}$alkoxy, $C_{1-5}$acyloxy, F, azido, and amino; or one of $R^4$ and $R^5$ is F and the other is selected from the group consisting of azido and amino; and $R^6$ is selected from the group consisting of hydrogen, $P(O)(OH)_2$ and alkali or alkaline earth metal salts thereof.

BRIEF DESCRIPTION OF THE DRAWINGS

The synthesis of the compounds of this invention is illustrated in FIGS. 1 through 6 in which R of FIG. 2 is equivalent to $R^4$ of Formula X and R' of FIG. 6 is equivalent to $R^5$ of Formula X.

DETAILED DESCRIPTION OF THE INVENTION

The principal feature of the compounds of this invention is that the glucose moiety of the etoposide has been replaced with altrose.

Figure 1:
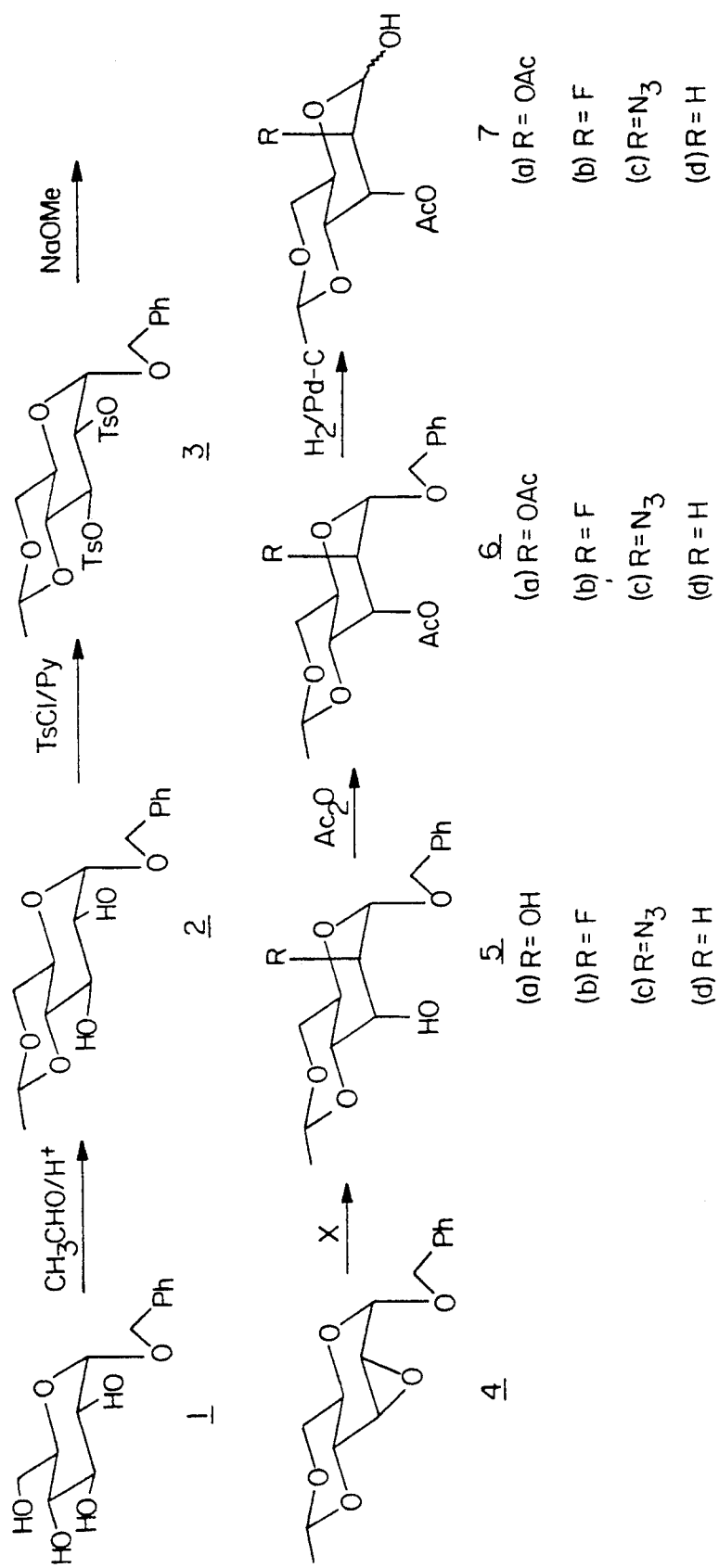

As will be seen from FIG. 1, the synthesis proceeds through compound 4, benzyl 2,3-anhydro-4,6-O-ethylidene-α-D-allopyranoside which is prepared from benzyl α-D-glucopyranoside or the corresponding ($C_1$-$C_{10}$) alkyl, phenyl, furyl or 2-thienyl compounds, all of which are known or can be prepared by known reactions, by acetal formation followed by tosylation and formation of the epoxide 4 by reaction with an alkali metal lower alkoxide in a lower alkanol solvent.

Figure 2:
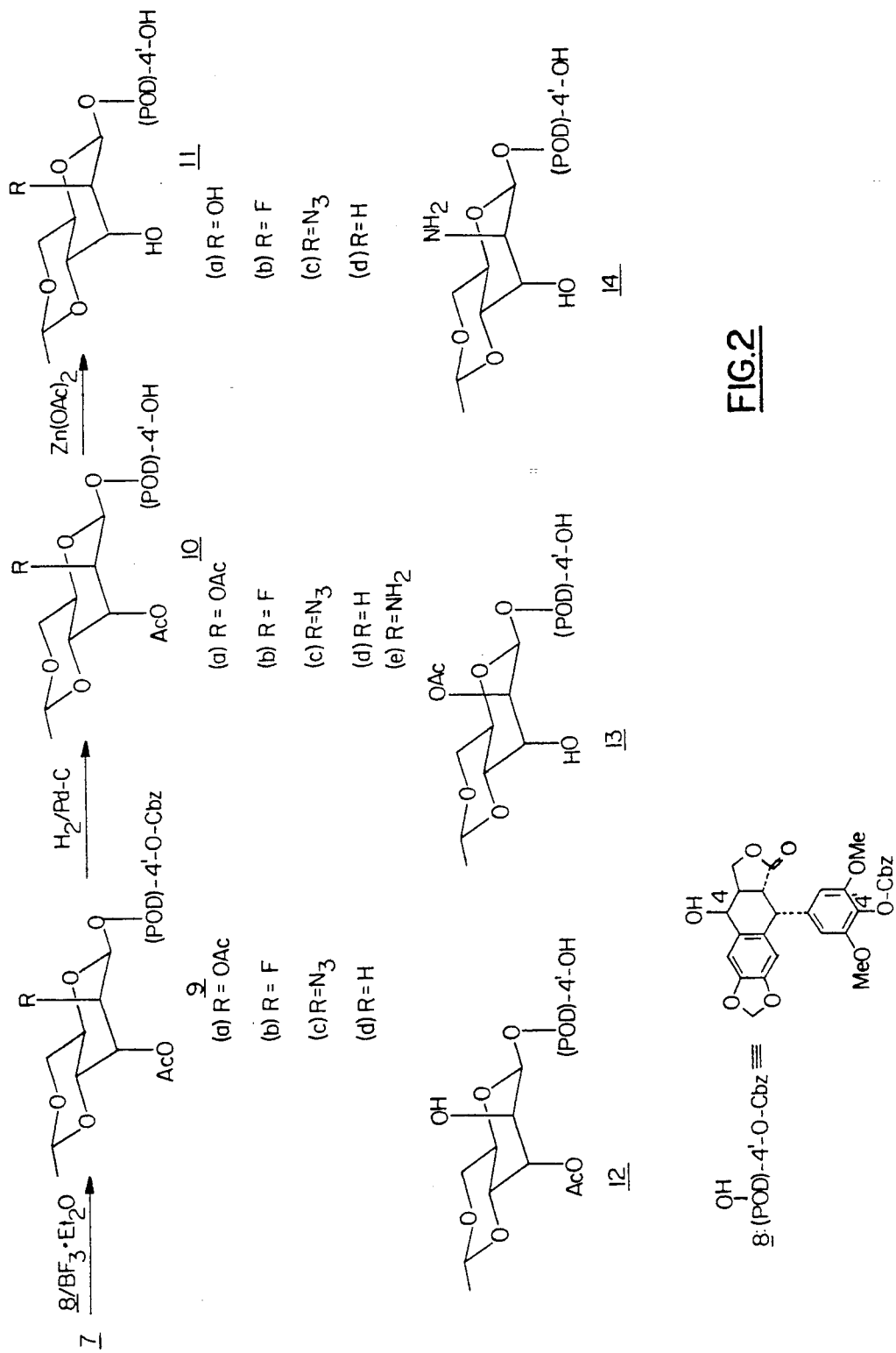

Compounds 1 through 7 of FIG. 1 may be considered starting materials. The compounds in FIG. 2 are either within the scope of the invention or they are novel intermediates for the preparation of such compounds.

The starting compound in the illustrative synthesis of the compounds of this invention as shown in the figures is the known compound benzyl α-D-glucopyranoside which is ethylidenated with acetaldehyde in the presence of an acid catalyst. The reaction is carried out in a reaction inert organic solvent such as methylene chloride, ethylene chloride, acetonitrile, tetrahydrofuran, or mixtures thereof. Suitable acid catalysts include hydrochloric acid, sulfuric acid, toluene sulfonic acid, or a Lewis acid such as zinc chloride. The reaction temperature may be from about 10° C. to about 50° C., preferably ambient temperature for a period of from about 1 to 4 days.

Tosylation may be effected by reaction with p-toluenesulfonyl chloride in an anhydrous organic solvent in the presence of a nitrogenous base to neutralize the HCl produced. Preferably, the reaction is conducted in dry pyridine at a temperature of from about 20° C. to 40° C., suitably ambient temperature for a period of from about 3 to 7 days.

The tosylated compound is converted to compound 4 by reaction with an alkali metal alkoxide in a lower alkanol, suitably sodium or potassium methoxide or ethoxide in methanol or ethanol. A reaction inert organic solvent such as an ester or an ether may be employed. Alternatively an excess of the alkanol is utilized. The reaction period is from about 16 to 30 hours at about 20° C. to 40° C.

The epoxide ring is opened to form the 2'-hydroxy compound by heating in a reaction inert, organic solvent, suitably an ether such as tetrahydrofuran or dioxane at a temperature of from about 60° C. to 120° C. for a period of from about 1 to 3 days.

Acylation to form a compound such as 6a is effected with an acylating agent, preferably an anhydride such as acetic anhydride in the presence of a nitrogenous base. Anhydrous pyridine is the preferred base, and it is normally employed in excess so that it also serves as the solvent. The reaction temperature is from about 20° to 40° C., suitably ambient temperature. The period of reaction is from about 30 minutes to 3 hours.

Hydrogenolysis is typically conducted with hydrogen in the presence of a palladium catalyst, suitably palladium on carbon or barium sulfate. Typically, a mixed solvent comprising a lower alkanol and a lower carboxylic acid is employed. Methanol or ethanol together with acetic acid are preferred. Although pressure may be employed, the reaction is usually carried out at atmospheric pressure at a temperature of from about 20° to 40° C. during a period of about 1 to 3 days. The compounds designated 7a, b, and d in FIG. 1 were prepared by this procedure.

The fluorinated compound, 5b, was prepared by treatment of the common intermediate 4 with an alkali metal hydrogen fluoride according to the method of Wright et al, J. Org. Chem., 34, 2632 (1969). The reaction may be carried out in the presence of a molar excess of potassium hydrogen fluoride in a high boiling reaction inert organic solvent, suitably an organic polyol such as ethylene glycol. The reaction period from about 1.5 to 3 hours at a temperature of from about 175° to 300° C., preferably for a period of from about 30 minutes to one hour.

The fluorinated compound 5b is acetylated as described above to form 6b which is then debenzylated to form the mixture of isomers 7b by hydrogenation with, for example hydrogen over palladium on carbon.

Compound 4 is converted to the azide 5c by reaction with an alkali metal azide, preferably sodium azide in a reaction inert, anhydrous organic solvent such as dimethyl formamide, dimethyl sulfoxide or tetrahydrofuran at a temperature of from about 90° to 125° C. for a period of 1 to 3 days.

The compound may be acylated as described above to form compound 6c.

It was observed that debenzylation of 6c by hydrogenation did not give a clean product. Therefore, the method of Hashimoto as described in Tetrahedron Letters, 28 3505 (1987) was utilized to prepare 3-O-acetyl-2-azido-2-deoxy-4,6-O-ethylidene α and β-D altropyranose, 7c.

In this procedure, the benzylated compound is first reacted with a molar excess of N-bromosuccinimide and propylene oxide in a halogenated organic solvent such as carbon tetrachloride or chloroform, or a mixture of these during a period of about 1 to 3 hours at about 75° to 100° C. The resulting product is next reacted with a molar excess of $Hg(CN)_2$ in reaction inert, oxygenated organic solvent miscible with water, suitably aqueous acetone at about 20° C. to 40° C. for from about 30 minutes to 2 hours.

Compound 5d may be prepared by reduction of compound 4 for example with sodium borohydride or lithium aluminum hydride in an anhydrous organic solvent such as ether, dioxane or tetrahydrofuran at about 30° to 75° C. for one to three hours.

The acetylated product, 6d may be prepared by acetylation of 5d with acetic anhydride and thereafter hydrogenated to form compound 7d using the procedures described above.

All altrose derivatives (7a to 7d) are isolated as mixtures of α and β anomers.

The epipodophyllotoxins of the invention are prepared by condensation of the selected altrose derivative, 7a to 7d prepared as described above with 4'-benzyloxycarbonyl-4'-demethylepipodophyllotoxin, compound 8, or with an analogous compound in which the phenol group is protected.

The condensation reaction is carried out in a reaction inert organic solvent, for example methylene or ethylene chloride at a temperature below 0° C., and in the presence of a catalyst such as boron trifluoride-ethyl etherate. The reaction time may be from about 10 minutes to about 5 hours, preferably from about 30 minutes to 1.5 hours. The reaction with boron trifluoride ethyl etherate may be quenched by the addition to the reaction mixture a tertiary amine such as pyridine or triethylamine. The choice of the phenol protecting groups is not particularly restricted and may include the formation of acyl derivatives, such as esters, as well as carbonates, ethers, acetals, and the like. These protecting groups may be removed using conventional deblocking methods, the choice of which depends on the nature of the protecting groups employed. Typical methods that may be mentioned include hydrogenation, acid or base catalyzed hydrolysis, and alcoholysis in the presence of a metal catalyst such as zinc powder or zinc acetate.

In the procedure illustrated in FIG. 2, the phenol protecting group is the carbobenzoxy group. It is removed by hydrogenation utilizing the procedures described above, preferably hydrogenation using hydrogen over palladium on carbon.

It has been observed that glycosidation of anomeric mixtures of altrose derivatives 7a to 7d gives predominantly the β-anomers. This high stereoselectivity is believed to be associated with 1,3-diaxial steric interaction between the 3-acetoxy and 1-hydroxy groups which impedes glycosidation with the α-isomer, but not with the β-isomer.

Deacetylation of compound 10a with zinc acetate in hot ethanol provides a mixture of starting compounds, namely the 2''-O-acetyl derivative 13, the 3''-O-acetyl derivative 12 and the completely deacetylated compound 11a which may be separated by chromatography over silica gel.

Compounds 11b to 11d are similarly prepared with zinc acetate in alkanol from compounds 10b to 10d.

Catalytic reduction of the azido compounds 10c and 11c for a prolonged period and/or in acetic acid converts the 2''-azido group to the amino group and provides compounds 10e, 4'-demethyl-4-O-(3-O-acetyl-2-amino-2-deoxy-4,6-O-ethylidene-β-D-altropyranosyl)epipodophyllotoxin, and 14, 4'-demethyl-4-O-(2-amino-2-deoxy-4,6-O-ethylidene-β-D-altropyranosyl)epipodophyllotoxin, respectively. Hydrogenation may be effected with hydrogen over palladium on carbon as described above.

Figure 3:
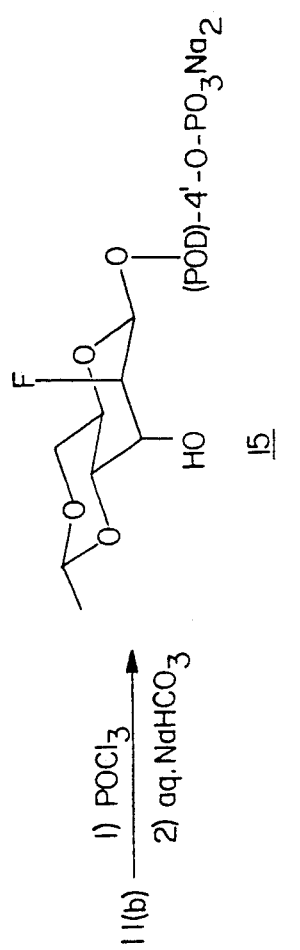

The 4'-phosphorylated compounds of the invention are formed by reaction of a deprotected phenol with a phosporylating agent such as phosphorous oxychloride or pyrophosphoric acid, preferably the former. The reaction with the oxychloride is similar to the tosylation reaction. It takes place in a reaction inert organic solvent in the presence of a nitrogenous base which will neutralize the acid produced. Tertiary amines are preferred including pyridine, dialkyl aromatic amines and trialkyl amines. FIG. 3 illustrates the conversion of compound 11b to compound 15, the disodium phosphate.

The reaction is conducted at about 0° to 20° C. during a period of from about 5 to 30 minutes. The acid may be isolated if desired, but it is preferred to convert directly to the salt in situ, by the addition of a metallic base, suitably an alkali metal carbonate, bicarbonate or hydroxide. The bicarbonate is preferred.

Figure 4:
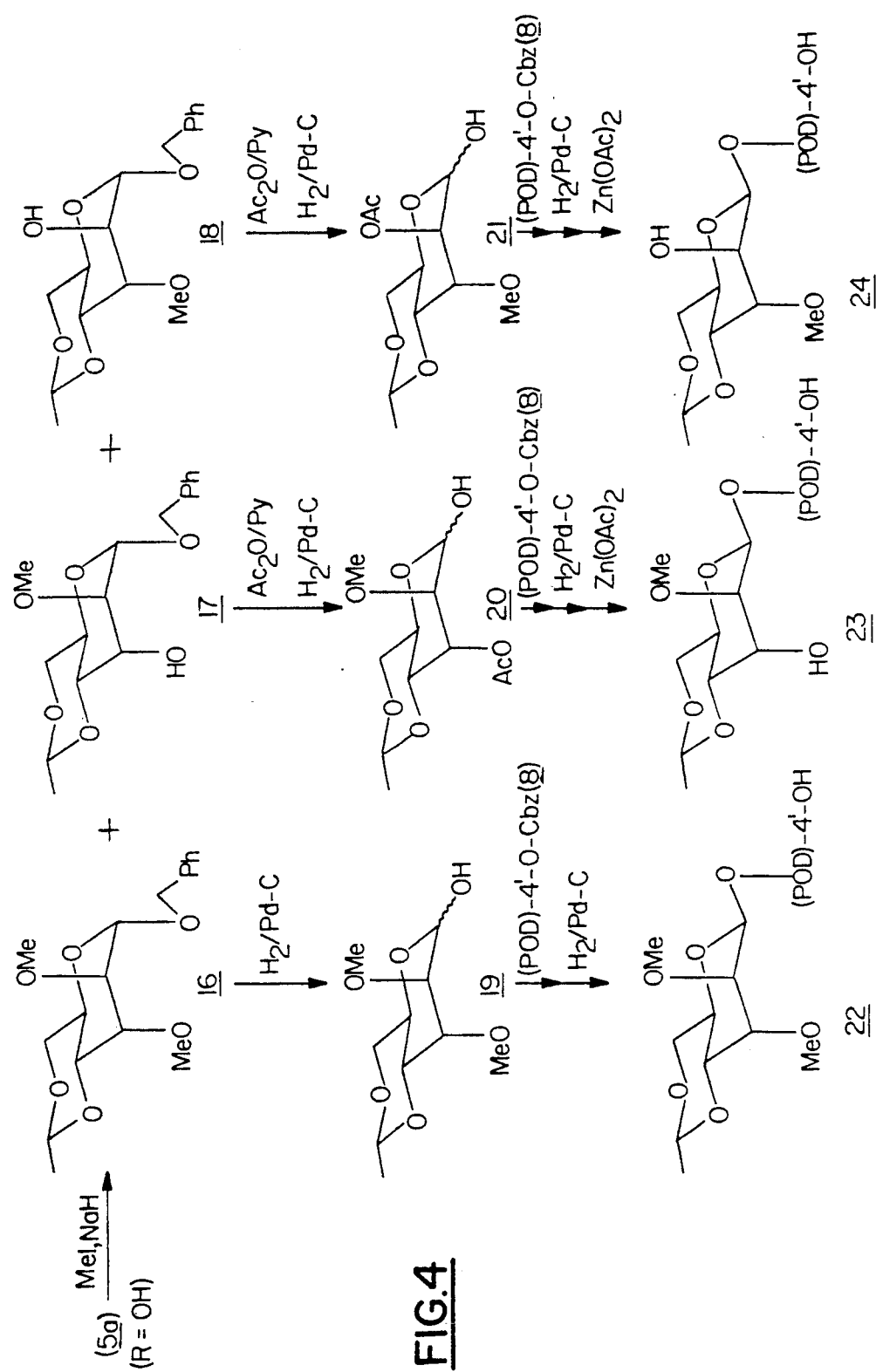

The 2'' and/or 3''-O-alkyl analogs of the etoposides, for example the methyl analogs, compounds 22, 23 and 24 are prepared as shown in FIG. 4.

In the first step of the synthesis, benzyl 4,6-O-ethylidene-α-D-altropyranoside, compound 5a, is alkylated at ambient temperature, i.e. about 25° C. to 40° C. in a polar solvent such as dimethyl sulfoxide (DMSO) or dimethyl formamide (DMF) employing a mixture of an alkali metal hydroxide such as sodium hydroxide and an alkyl iodide such as methyl iodide. The reaction time is about 15 to 60 minutes. A slight molar excess of hydroxide and iodide may be employed, but equimolar quantities are normally sufficient.

There results, when methyl iodide is used, a mixture of isomers, namely benzyl-2,3-di-O-methyl-4,6-O-ethylidene-α-D-altropyranoside, compound 16; benzyl 4,6-O-ethylidene-2-O-methyl-α-D-altropyranoside, compound 17; and benzyl 4,6-O-ethylidene-3-O-methyl-α-D-altropyranoside, compound 18. They may be separated and isolated chromatographically as illustrated in the examples.

Compound 16 may be converted to compound 22, 4'-demethyl-4-O-(2,3-di-O-methyl-4,6-O-ethylidene-β-D-altropyranosyl)epipodophyllotoxin by reduction followed by condensation with 4'-demethyl-4'-benzyloxycarbonylepipodophyllotoxin and a second reduction using the procedures described hereinabove, illustrated in the examples and shown in FIG. 4.

The compound 4'-demethyl-4-O-(4,6-O-ethylidene-2-O-methyl-β-D-altropyranosyl)epipodophyllotoxin, compound 23 was prepared as shown in FIG. 4, i.e. acetylation, reduction, condensation, reduction and reaction with zinc acetate. All of the procedures are described above and illustrated in the examples.

Compound 24, 4'-demethyl-4-O-(2-O-acetyl-4,6-O-ethylidene-3-O-methyl-β-D-altropyranosyl)epipodophyllotoxin was prepared from compound 18 by the series of reactions shown in FIG. 4. The reactions are described above and illustrated in the examples. They are acetylation, reduction, condensation, reduction and, as the last step, reaction with zinc acetate.

Figure 5:
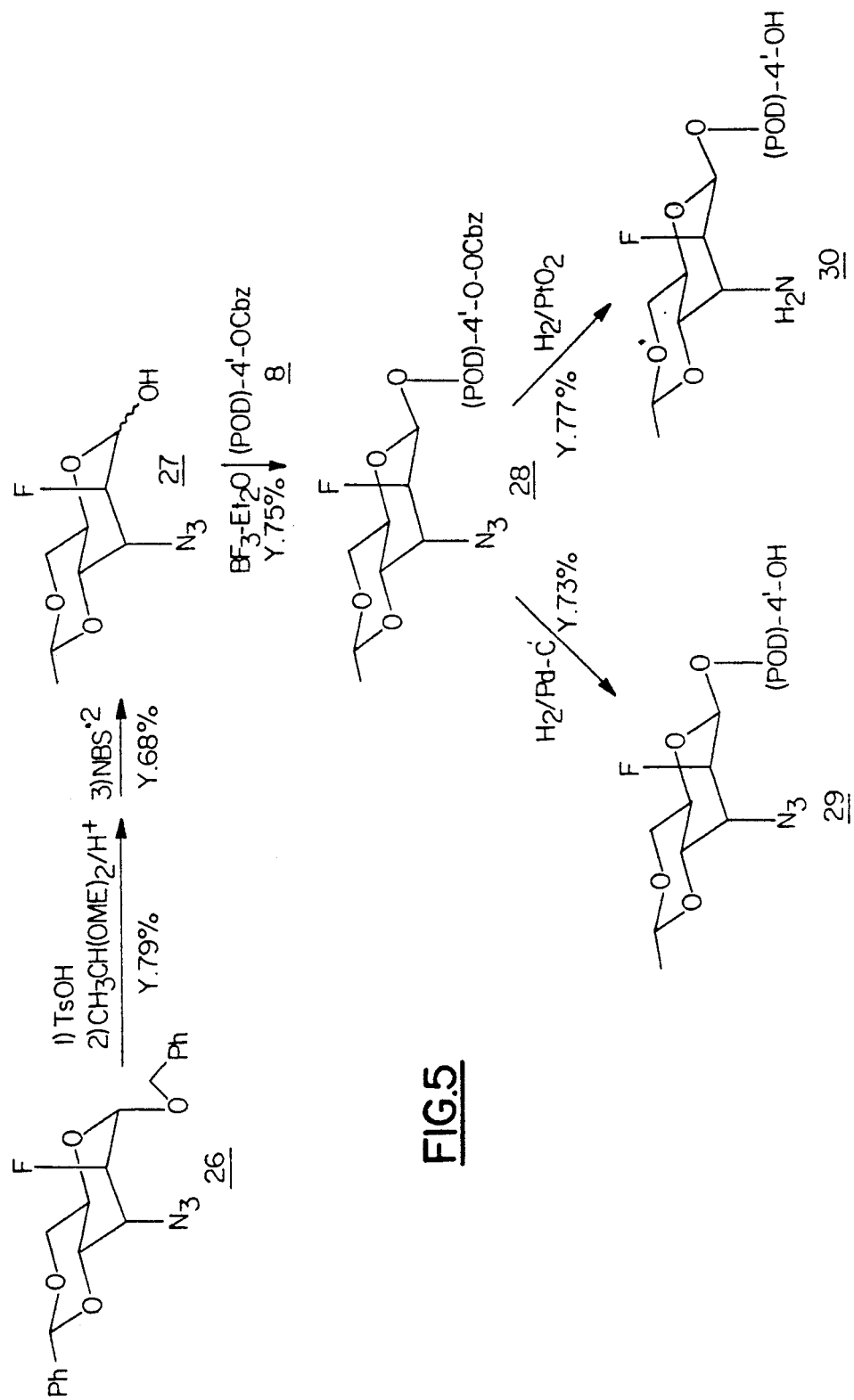

FIG. 5 illustrates the preparation of two additional active compounds of this invention, namely 4'-demethyl-4-O-(3-azido-4,6-O-ethylidene-2-fluoro-β-D-altropyranosyl)epipodophyllotoxin and 4'-demethyl-4-O-(3-amino-4,6-O-ethylidene-2-fluoro-β-D-altropyranosyl)-epipodophyllotoxin.

The compounds are prepared from the known compound 3-azido-2,3-dideoxy-4,6-O-ethylidene-2-fluoro-α-D-altropyranose. See S. Castillon, et al., J. Org. Chem., 50, 4913 (1985). The reactions are shown in the figure and illustrated in the examples. The reactions are conducted generally as described above except for the reduction of compound 28 to form the compound 30.

For the formation of compound 30, the catalyst employed for the hydrogenation is platinum oxide instead of palladium on carbon. The reaction is typically conducted at ambient temperature, i.e., 20° C. to 45° C. using a molar excess of hydrogen in an acid solvent, e.g. acetic acid: water.

As will be seen in the figure and understood from the examples, the reduction of compound 28 using a platinum oxide catalyst results not only in the reduction of the azido group, but also removal of the carbobenzoxy group.

Figure 6:
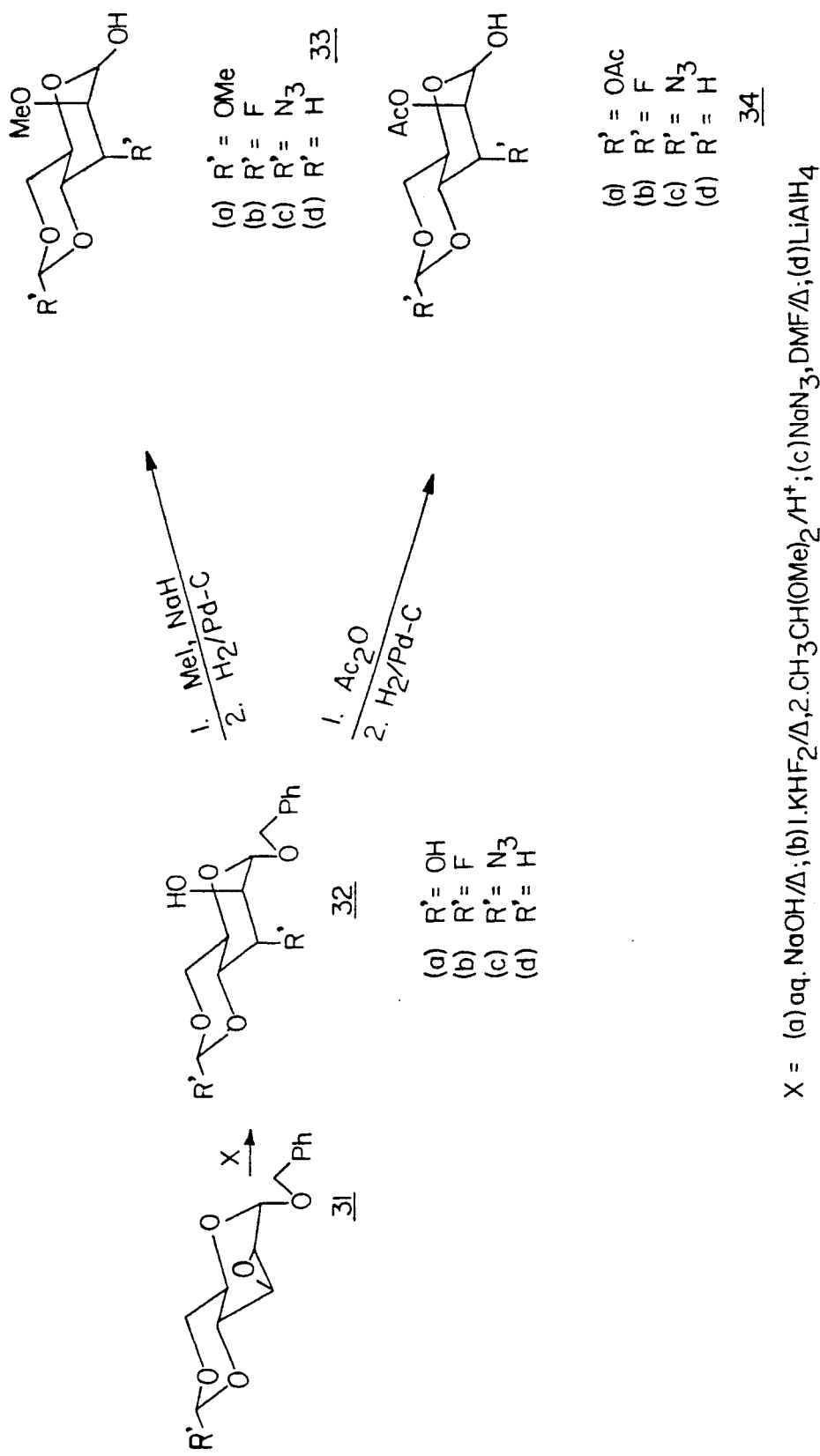

FIG. 6 is analogous to the sequence illustrated in FIG. 1 which shows the conversion of compound 4 of FIG. 1 to compounds 5(a–d), 6(a–d) and 7(a–d) except that in FIG. 6, compound 4 is replaced with benzyl 2,3-anhydro-α-mannopyranoside-4,6-O-cyclic acetal prepared according to the procedure of Robertson, G. J., et al, J. Chem. Soc., 1935, 1193-1201. The corresponding ($C_1$–$C_{10}$)alkyl, phenyl, furyl and 2-thienyl compounds are known or can be prepared by known reactions.

The reactions of FIG. 6 are carried out using the procedures described in connection with the reactions of FIG. 1, except that in the methylation reaction, the procedure is as described in connection with FIG. 4. Subsequent reactions to form products of the invention are in accordance with the procedures shown in FIG. 2 and described above.

Additional products of the invention are prepared from the compounds of FIG. 6 using the procedures described in connection with FIGS. 2, 3 and 4. They are all illustrated in the examples.

The compounds prepared as described above are isolated and purified by any of the procedures well known to the art including, for example extraction, precipitation, crystallization and chromatography all of which are illustrated in the examples together with a number of other methods.

BIOLOGICAL ACTIVITY

Representative compounds of the present invention were evaluated for antitumor activity against murine transplantable P388 leukemia. Five-week old female $CDF_1$ mice were inoculated intraperitoneally with 0.4 ml of diluted ascitic fluid containing $10^6$ lymphocytic leukemia P388 cells. Test compounds were administered intraperitoneally as a single dose on day 1 and animals were observed for 45 days. The percent increase of median survival time (MST) of treated animals over that of untreated control animals was determined and reported as % T/C. Compounds showing % T/C values of 125 or greater are considered to have significant antitumor activity. Table I presents the results of the in vivo evaluation in terms of the maximum % T/C (accompanied with the dose giving the maximum effects in parenthesis), and the minimum effective dose (MED) which indicates the minimum dose giving a % T/C value of 125 or greater.

TABLE 1

ANTITUMOR ACTIVITY AGAINST P388 LEUKEMIA

| Compound | Max. % T/C of MST (Dose, mg/kg/day) | MED (mg/kg/day) |
| --- | --- | --- |
| Etoposide | 288 (120) | 0.3 |
| 10a | 170 (120) | 30 |
| 10b | 152 (60) | 10 |
| 10c | 150 (120) | 30 |
| 10d | 135 (120) | 120 |
| 11a | 220 (30) | 0.3 |
| 11b | 181 (60) | 3 |
| 11c | 139 (120) | 60 |
| 11d | 145 (120) | 30 |
| 12 | 190 (30) | 0.3 |
| 13 | 160 (120) | 10 |
| 14 | 176 (10) | 0.3 |
| 15 | 185 (120) | 30 |
| 22 | 160 (120) | 10 |
| 23 | 170 (120) | 30 |
| 24 | 180 (60) | 1 |
| 29 | 133 (30) | 30 |
| 30 | 152 (30) | 30 |

Accordingly, the present invention provides a method for inhibiting mammalian tumors which comprises administering an effective tumor-inhibiting dose of an antitumor compound of Formula III to a tumor bearing host. For this purpose, the drug may be administered by conventional routes including, but not limited to, intravenous, intramuscular, intratumoral, intraarterial, intralymphatic, and oral.

A further aspect of the present invention provides a pharmaceutical composition which comprises a compound of Formula III and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug and are well understood by those skilled in the art will be taken into account including age, weight, sex, diet, time of administration, route of administration, rate of excretion, condition of the patient, drug combinations, reaction sensitivities and severity of the disease.

The following examples are for illustrative purposes only and should not be construed as limiting the scope of the invention which is defined solely by the Claims appended to this application.

PREPARATION OF STARTING MATERIALS

Benzyl 4,6-O-ethylidene-α-D-glucopyranoside (2)

To a suspension of benzyl α-D-glucopyranoside (1) (22 g, 0.0815 mol) and acetaldehyde (20 ml) in dry methylene chloride (250 ml) was added 2 drops of concentrated sulfuric acid, and the mixture was stirred vigorously at room temperature for 3 days. The reaction mixture was washed successively with aqueous $NaHCO_3$ solution, water and brine, and dried over $MgSO_4$. After removal of the solvent, the oily residue was chromatographed on a silica gel column (Wako gel C-200, 250 g). The column was eluted with chloroform and then chloroform-methanol (50:1-25:1). Fractions containing the desired product were collected and evaporated to dryness to give an oily residue, which was triturated with isopropyl ether to give 19.22 g (80%) of the title compound (2). MP 110°-118° C. IR$\nu_{max}$ (KBr) cm$^{-1}$ 1173, 1160, 1150, 1127. $^1$H NMR (CDCl$_3$) δ1.37 (3H, d, J=5.13 Hz, CH—CH$_3$), 4.72 (1H, q, J=5.13 Hz, CH—CH$_3$), 4.98 (1H, d, J=4.03 Hz, H-1).

Anal: Calcd for $C_{15}H_{20}O_6$: C 60.80, H 6.80. Found: C 60.90, H 6.92.

Benzyl 2,3-bis-(O-p-toluenesulfonyl)-4,6-O-ethylidene-α-D-glucopyranoside (3)

To a solution of 2 (29 g, 0.1 mol) and 4-dimethylaminopyridine (24.4 g, 0.2 mol) in dry pyridine (300 ml) was added p-toluenesulfonyl chloride (76 g, 0.4 mol) and the mixture was stirred at room temperature for 3 days. To the mixture was added an additional 38 G (0.2 mol) of p-toluenesulfonyl chloride and the mixture was stirred again for 4 days. Most of the solvent was removed under reduced pressure. The residue was poured into 1 L of water and the mixture extracted with 1 L of methylene chloride. The extract was washed successively with 500 ml of 2N sulfuric acid, water and brine, and dried over MgSO$_4$. The dried extract was evaporated in vacuo and the oily residue was triturated with 500 ml of ether to give 11.9 g of the title compound (3). The filtrate was concentrated and the concentrate was chromatographed on a silica gel column (Wako gel D-200, 300 g). The column was eluted with chloroform and chloroform-methanol (50:1-10:1). The fractions containing 3 were collected and evaporated to dryness to give 7.7 g of 3 as a second crop. The total yield of 3 was 19.6 g (32.5%). MP 140°-42° C. IR $\nu$max (KBr) cm$^{-1}$ 1600, 1366, 1347, 1183, 1178. $^1$H NMR (CDCl$_3$) δ0.98 (3H, d, J=5.13 Hz, CH—CH$_3$), 2.40 (3H, s, CH$_3$Ph), 2.44 (3H, s, CH$_3$Ph), 4.39 (1H, dd, J=9.52 and 3.66 Hz, H-2), 4.40 (1H, q, J=5.13 Hz, CH—CH$_3$), 4.98 (1H, dd, J=9.89 and 9.52 Hz H-3), 5.20 (1H, d, J=3.66 Hz, H-1).

Anal: Calcd for C$_{29}$H$_{32}$O$_{10}$S$_2$: C 57.60, H 5.33, S 10.60. Found: C 57.52, H 5.31, S 10.60.

Benzyl 2,3-anhydro-4,6-O-ethylidene-α-D-allopyranoside (4)

To a solution of 3 (15.3 g, 0.0253 mol) in ethyl acetate (300 ml) was added 28% sodium methoxide in methanol (20 ml, 0.1 mol) and the mixture was stirred at room temperature for 24 hours. The reaction mixture was washed with water and brine, and dried over MgSO$_4$. After evaporating to dryness, the residue was triturated with ether-n-hexane to give 4.31 g of the title compound (4). The filtrate was evaporated to dryness and the residue was chromatographed on a silica gel column (Kiesel gel 60, 40 g). The column was eluted with toluene-ethyl acetate (10:1) and the desired fractions were collected and evaporated to dryness to give 1.45 g of 4. The total yield of 4 was 5.76 g (82%). MP 132°-134° C. IR $\nu$max (KBr) cm$^{-1}$ 1170, 1153, 1119, 1055, 1034. $^1$H NMR (CDCl$_3$) δ1.38 (3H, d, J=5.13 Hz, CH—CH$_3$), 3.37 (1H, d, J=4.40 Hz, H-3), 3.46 (1H, dd, J=4.40 and 1.10 Hz, H-2), 4.79 (1H, q, J=5.13 Hz, CH—CH$_3$), 5.04 (1H, d, J=1.10 Hz, H-1).

Anal: Calcd for C$_{15}$H$_{18}$O$_5$: C 64.74, H 6.52. Found: C 64.51, H 6.50.

Benzyl 4,6-O-ethylidene-α-D-altropyranoside (5a and 32a)

To a solution of 4 (3.06 g, 11 mmol) in dioxane (100 ml) was added 1N sodium hydroxide (100 ml, 100 mmol) and the mixture was refluxed with stirring for 2 days. The reaction mixture was concentrated to 100 ml and the concentrate was extracted with 300 ml of chloroform. The extract was washed with water and brine, and dried over MgSO$_4$. After removal of the solvent, the oily residue was chromatographed on a silica gel column (Kiesel gel 60, 50 g). The column was eluted with toluene-ethyl acetate (10:1-1:1). The desired fractions eluted with toluene-ethyl acetate (1:1) were collected and evaporated to dryness to give 2.53 g (78%) of the title compound (5a). MP 116°-118° C. IR$\nu_{max}$ (KBr) cm$^{-1}$ 3450, 3300, 1412, 1132. $^1$H NMR (CDCl$_3$) δ1.38 (3H, d, J=5.13 Hz, CH—CH$_3$), 4.83 (1H, q, J=5.13 Hz, CH—CH$_3$), 4.81 (1H, br.s, H-1).

Anal: Calcd for C$_{15}$H$_{20}$O$_6$: C 60.80, H 6.80. Found: C 60.53, H 6.81.

This compound is similarly prepared as compound 32a from benzyl 2,3-anhydro-4,6-O-ethylidene-α-D-mannopyranoside (Compound 31 of FIG. 6).

Benzyl 2,3-di-O-acetyl-4,6-O-ethylidene-α-D-altropyranoside (6a)

A mixture of 5a (2.5 g, 8.4 mmol) and 4-dimethyl aminopyridine (250 mg) in dry pyridine (25 ml) and acetic anhydride (10 ml) was stirred at room temperature for 1 hour. To the reaction mixture was added 10 ml of MeOH and the solution was stirred at room temperature for 30 min. The mixture was concentrated under reduced pressure and the residue, diluted with 100 ml of ethyl acetate, was washed successively with 5% sulfuric acid, water, a saturated aqueous NaHCO$_3$ solution, and brine, and dried over MgSO$_4$. The dried extract was evaporated to dryness and the residue was chromatographed on a silica gel column (Kiesel gel 60, 40 g). The column was eluted with toluene-ethyl acetate (10:1) and the desired fractions were collected and evaporated to dryness to give 2.55 g (80%) of the title compound (6a). MP 94°-96° C. IR$\nu_{max}$ (KBr) cm$^{-1}$ 1746, 1733, 1240, 1221, 1136. $^1$H NMR (CDCl$_3$) δ1.34 (3H, d, J=5.13 Hz, CH—CH$_3$), 2.05 (3H, s, OCOCH$_3$), 2.07 (3H, s, OCOCH$_3$), 4.78 (1H, d, J=1.10 Hz, H-1), 4.79 (1H, q, J=5.13 Hz, CH—CH$_3$), 5.09 (1H, dd, J=2.93 and 1.10 Hz, H-2), 5.11 (1H, t, J=2.93 Hz, H-3).

Anal: Calcd for C$_{19}$H$_{24}$O$_8$: C 59.99, H 6.36. Found: C 60.03, H 6.43.

2,3-Di-O-acetyl-4,6-O-ethylidene-altropyranose (7a and 34a)

A mixture of 6a (1.14 g, 3 mmol) and 10% palladium on carbon (1 g) in acetic acid (50 ml) and ethanol (5 ml) was hydrogenated under one atmosphere pressure for 2 days. The catalyst was removed by filtration and washed with methanol. The filtrate and washings were evaporated to dryness and the residue was chromatographed on a silica gel column (Kiesel gel 60, 40 g). The column was eluted with toluene-ethyl acetate (10:1-1:1). The desired fractions eluted with toluene-ethyl acetate (1:1) were collected and evaporated to dryness to give 800 mg (92%) of 7a as a mixture of α and β-isomers. MP ca. 55° C. IR$\nu$max (KBr) cm$^{-1}$ 1752, 1374, 1229. $^1$H NMR (CDCl$_3$) δ5.04 (1H, d, J=6.60 Hz, H-1 of α-isomer), 5.16 (1H, dd, J=8.80 and 1.46 Hz, H-1 of β-isomer).

Anal: Calcd for C$_{12}$H$_{18}$O$_8$: C 49.65, H 6.25. Found: C 49.43, H 6.46.

This compound is identical with compound 34a of FIG. 6 which was prepared in the same manner.

Benzyl 2-deoxy-4,6-O-ethylidene-2-fluoro-α-D-altropyranoside (5b)

A mixture of 4 (10 g, 0.036 mol) and potassium hydrogen fluoride (25 g, 0.32 mol) in ethylene glycol (200 ml) was heated at 200° C. for 45 min with stirring. After cooling to room temperature, the reaction mixture was extracted with 500 ml of chloroform and the extract was washed with aqueous NaHCO$_3$ and dried over MgSO$_4$. The dried extract was concentrated to 200 ml. To the concentrate was added acetaldehyde dimethylacetal (19 ml, 0.18 mol) and p-toluene sulfonic acid (200 mg) and the mixture was stirred at room temperature for 20 hours. The mixture was washed with an aqueous NaHCO$_3$ solution, water and brine successively, and dried over MgSO$_4$. After removal of the solvent, the oily residue was chromatographed on a silica gel column (Kiesel gel 60, 130 g). The column was eluted with toluene-ethyl acetate (10:1) and the desired first fractions were collected and evaporated to dryness to give 3 g (28%) of the title compound (5b) as an oil. The second fractions were evaporated to dryness to give 1.03 g (9.6%) of benzyl 3-deoxy-4,6-O-ethylidene-3-fluoro-α-D-glucopyranoside. IR$\nu_{max}$ (liq.) cm$^{-1}$ 3500, 1500, 1460, 1420, 1220, 1160, 1140. $^1$H NMR (CDCl$_3$) δ1.38 (3H, d, J=5.13 Hz, CH—CH$_3$), 4.22 (1H, dt, J=6.60 and 2.93 Hz, H-3), 4.67 (1H, ddd, J=43.97, 3.30 and 1.10 Hz, H-2), 4.83 (1H, q, J=5.13 Hz, CH—CH$_3$), 4.95 (1H, d, J=10.26 Hz, H-1).

Compound 32b is similarly prepared from compound 31.

Benzyl 3-O-acetyl-2-deoxy-4,6-O-ethylidene-2-fluoro-α-D-altropyranoside (6b)

To a mixture of 5b (2.5 g, 8.39 mmol) and 4-dimethylaminopyridine (250 mg) in dry pyridine (25 ml) was added acetic anhydride (10 ml) and the mixture was stirred at room temperature for 30 min. To the mixture was added 20 ml of methanol and the mixture was stirred at room temperature for 30 min and evaporated to dryness. The residue was diluted with 150 ml of ethyl acetate, washed with 5% sulfuric acid, water, aqueous NaHCO$_3$ solution, water and brine successively, and dried over MgSO$_4$. The dried extract was evaporated to dryness and the oily residue was chromatographed on a silica gel column (Kiesel gel 60, 40 g). The column was eluted with toluene-ethyl acetate (20:1) and the desired fractions were collected and evaporated to dryness to give 2.57 g (90%) of the title compound 6b as an oil. IR$\nu_{max}$ (liq.) cm$^{-1}$ 1750, 1500, 1410, 1380. $^1$H NMR (CDCl$_3$) δ1.35 (3H, d, J=5.13 Hz, CH—CH$_3$), 2.05 (3H, s, OCOCH$_3$), 4.75 (1H, ddd, J=43.23, 3.30 and 1.10 Hz, H-2), 4.80 (1H, q, J=5.13 Hz, CH—CH$_3$), 4.94 (1H, d, J=10.99 Hz, H-1), 5.27 (1H, dt, J=6.23 and 3.30 Hz, H-3).

The corresponding 3-fluoro compound is similarly prepared from compound 32b.

3-O-Acetyl-2-deoxy-4,6-O-ethylidene-2-fluoro-α and β-D-altropyranose (7b)

A mixture of 6b (2.5 g, 7.35 mmol) and 10% palladium on carbon (2.5 g) in acetic acid (50 ml) was hydrogenated at room temperature for 24 hours under one atmosphere pressure. The catalyst was removed by filtration and washed with MeOH, and the filtrate and washings were evaporated to dryness. The residue was dissolved in 200 ml of chloroform and the solution was washed with an aqueous NaHCO$_3$ solution, water and brine successively, and dried over MgSO$_4$. After removal of the solvent, the oily residue was chromatographed on a silica gel column (Kiesel gel 60,60 g). The column was eluted with chloroform and chloroform-methanol (50:1). The first fractions eluted with chloroform-methanol were collected and evaporated to dryness to give 800 mg (32%) of the recovered starting material (6b) as an oil. The second fractions were collected and evaporated to dryness to give 910 mg (49.5%) of the title compound (7b) as an oil. IR$\nu_{max}$ (liq.) cm$^{-1}$ 3450, 1750, 1420, 1380. $^1$H NMR (CDCl$_3$) δ1.33 and 1.34 (each 3H, d, J=5.13 Hz, CH—CH$_3$), 2.15 (6H, s, OCOCH$_3$), 4.75 and 4.79 (each 1H, q, J=5.13 Hz, CH—CH$_3$), 4.69 (1H, ddd, J=43.2, 3.30 and 1.10 Hz, H-2, α), 4.57 (1H, ddd, J=45.43, 3.66 and 0.73 Hz, H-2, β), 5.21 (1H, dd, J=10.63 and 6.23 Hz, H-1, α), 4.99 (1H, dd, J=20.52 and 11.73 Hz, H-1, β), 5.38 (1H, dd, J=5.50 and 3.30 Hz, H-3, α), 5.51 (1H, dd, J=7.33 and 3.30 Hz, H-3, β).

The corresponding compound, 34b, is similarly prepared from the 3-fluoro compound of the previous preparation.

Benzyl 2-azido-2-deoxy-4,6-O-ethylidene-α-D-altropyranoside (5c)

A mixture of 4 (11.12 g, 0.04 mol) and sodium azide (26 g, 0.4 mol) in dry DMF (200 ml) was heated at 100° C. for 2 days with stirring. The reaction mixture was concentrated to 50 ml and the concentrate was extracted with 800 ml of chloroform. The extract was washed with water and brine, and dried over MgSO$_4$. The dried extract was evaporated to dryness and the oily residue was chromatographed on a silica gel column (Kiesel gel 60, 130 g). The column was eluted with toluene-ethyl acetate (20:1). The desired fractions were collected and evaporated to dryness to give 10 g (78%) of the crude product 5c, which was used to the next acetylation without further purification. IR$\nu_{max}$ (liq.) cm$^{-1}$ 2100.

Compound 32c is similarly prepared from compound 31.

Benzyl 3-O-acetyl-2-azido-2-deoxy-4,6-O-ethylidene-α-D-altropyranoside (6c)

To a solution of crude 5c (10 g, 0.03 mol) in dry pyridine (100 ml) containing 4-dimethylaminopyridine (1 g) was added acetic anhydride (50 ml) and the solution was stirred at room temperature for 30 min. Methanol (50 ml) was added dropwise with cooling, the mixture stirred at room temperature for 30 min and evaporated to dryness. The residue was extracted with 500 ml of ethyl acetate and the extract was washed successively with 5% sulfuric acid, water and brine, and dried over MgSO$_4$. After removal of the solvent, the oily residue was chromatographed on a silica gel column (Kiesel gel 60, 100 g). The column was eluted with toluene-ethyl acetate (50:1-10:1). Fractions containing 6c were collected and chromatographed repeatedly (4 times) on a silica gel column by eluting with the same solvent. The first fractions were collected and evaporated to dryness to give 2.16 g (19%) of the glucose derivative, which was crystallized on standing. MP 76°-80° C. IR$\nu_{max}$ (KBr) cm$^{-1}$ 2106, 1747.

Anal: Calcd for C$_{17}$H$_{19}$N$_3$O$_6$: C 56.51, H 5.30, N 11.63. Found: C 56.21, H 5.83, N 11.65.

The second fractions were similarly collected and evaporated to dryness to give 7.35 g (65%) of the altrose derivative (6c) which was crystallized form n-hexane. MP 56°-57° C. IR$\nu_{max}$ (KBr) cm$^{-1}$ 2109, 1736. $^1$H NMR (CDCl$_3$) δ1.35 (3H, d, J=5.1 Hz, 8-H) 2.03 (3H, s, OCOCH$_3$), 3.55 (1H, t, J=10.3 Hz, 6-Hax), 3.77 (1H, dd, J=2.9 and 9.5 Hz, 4-H), 4.05 (1H, dd, J=0.7 and 2.9 Hz, 2-H), 4.11 (1H, dd, J=5.1 and 10.3 Hz, 6-Heq), 4.20 (1H, ddd, J=5.5, 9.9 and 10.3 Hz, 5-H), 4.46 and 4.74 (2H, each d, CH$_2$Ph), 4.78 (1H, q, J=5.1 Hz, 7-H), 4.83 (1H, brs, 1-H), 5.07 (1H, t, J=2.9 Hz, 3-H).

Anal: Calcd for C$_{17}$H$_{19}$N$_3$O$_6$: C 56.51, H 5.30, N 11.63. Found: C 56.12, H 5.81, N 11.65.

The corresponding 3-azido compound is similarly prepared from compound 32c.

3-O-Acetyl-2-azido-2-deoxy-4,6-O-ethylidene-α and β-D-altropyranose (7c)

A mixture of (6c) (1.27 g, 3.5 mmol), N-bromosuccinimide (1.88 g, 10.6 mmol) and propylene oxide (7 ml) in carbon tetrachloride (30 ml) and chloroform (30 ml) was refluxed for 1.5 hours. The reaction mixture was evaporated to dryness and the residue was dissolved in 40 ml of acetone. To the solution was added a solution of mercury cyanide (1.76 g, 7.6 mmol) in water (20 ml), the mixture stirred at room temperature for one hour and concentrated to 20 ml. The concentrate was extracted with 100 ml of chloroform and washed with water and brine, and dried over MgSO$_4$. The dried extract was evaporated to dryness and the oily residue was chromatographed on a silica gel column (Kiesel gel 60, 50 g). The column was eluted with toluene-ethyl acetate (10:1–2:1) successively. The desired fractions eluted with toluene-ethyl acetate (2:1) were collected and evaporated to dryness to give 710 mg (67.5%) of 7c as an oil. IR νmax (Neat) cm$^{-1}$ 3300–3500, 2110, 1410, 1220, 1090, 1070. $^1$H NMR No peak due to the benzyl protons was observed.

The corresponding 3-azido compound, compound 34c, is similarly prepared from the 3-azido compound of the previous preparation.

Benzyl 2-deoxy-4,6-O-ethylidene-α-D-altropyranoside (5d)

To a stirred suspension of lithium aluminum hydride (5 g, 0.132 mol) in dry ether (200 ml) was added dropwise at reflux temperature a solution of 4, (3.17 g, 11.4 mmol) in 200 ml of dry ether, and the mixture was refluxed for 1.5 hours and cooled to 0° C. To the reaction mixture were added dropwise 50 ml of ethyl acetate, 50 ml of water and 150 ml of 2N sulfuric acid successively. The organic layer was separated and washed with water, brine and dried over MgSO$_4$. The dried extract was evaporated to dryness and the oily residue was chromatographed on a silica gel column (Kiesel gel 60, 80 g). The column was eluted with toluene-ethyl acetate (2:1). The desired fractions by monitoring with TLC, were collected and evaporated to dryness to give 3.13 g (98%) of 5d. MP 74°-76° C. IRνmax (KBr) cm$^{-1}$ 3550, 1165, 1149, 1125, 1100, 1056, 1034, 1026. $^1$H NMR (CDCl$_3$) δ1.39 (3H, d, J=5.1 Hz, H-8), 4.81 (1H, q, J=5.1 Hz, H-7), 4.95 (1H, d, J=3.8 H, H-1).

Compound 32d is similarly prepared from compound 31.

Benzyl 3-O-acetyl-2-deoxy-4,6-O-ethylidene-α-D-altropyranoside (6d)

A solution of 5d (3 g, 0.0107 mol) and 4-N,N-dimethylaminopyridine (0.3 g) in pyridine (60 ml) and acetic anhydride (30 ml) was stirred at room temperature for one hour. To the reaction solution was added dropwise 60 ml of methanol and the mixture was evaporated to dryness. The residue was extracted with 200 ml of ethyl acetate, washed successively with 2N sulfuric acid, water, brine, and dried over MgSO$_4$. After removal of the solvent, the oily residue was chromatographed on a silica gel column (Kiesel gel 60, 100 g). The column was eluted with toluene-ethyl acetate (10:1–5:1) successively. The desired fractions were collected and evaporated to dryness to give 2.65 g (77%) of 6d as an oil. $^1$H NMR (CDCl$_3$) δ1.35 (3H, d, J=5.1 Hz, 8-H), 1.96 (1H, ddd, J=3.0, 4.3 and 15.4 Hz, 2-Hax), 2.04 (3H, s, OCOCH$_3$), 2.36 (1H, ddd, J=0.9, 3.0 and 15.4 Hz, 2-Heq), 3.49 (1H, dd, J=3.0 and 9.8 Hz, 4-H), 3.50 (1H, t, J=10.3 Hz, 6-Hax), 4.09 (1H, dd, J=5.1 and 10.3 Hz, 6-Heq), 4.24 (1H, ddd, J=5.1, 9.8 and 10.3 Hz, 5-H), 4.42 and 4.73 (2H, each, d, CH$_2$Ph), 4.77 (1H, q, J=5.1 Hz, 7-H), 4.90 (1H, d, J=4.3 Hz, 1-H).

The corresponding 2-O-acetyl-3-deoxy compound is similarly prepared from compound 32d.

3-O-Acetyl-2-deoxy-4,6-O-ethylidene-α and β-D-altropyranose (7d)

A mixture of 6d (2.47 g, 7.67 mmol) and 10% palladium on carbon (1 g) in acetic acid (50 ml) and ethanol (10 ml) was hydrogenated under one atmosphere pressure for 20 hours. The catalyst was removed by filtration and the catalyst was washed twice with 50 ml of methanol. The filtrate and washings were combined and evaporated to dryness. The oily residue was chromatographed on a silica gel column (Kiesel gel 60, 100 g). The column was eluted with toluene-ethyl acetate (2:1). The desired fractions by monitoring with TLC, were collected and evaporated to dryness to give 1.32 g (74%) of 7d as an oil, which consisted of a 1:2 mixture of α and β-anomers on $^1$H-NMR spectrum.

The corresponding 2-O-acetyl-3-deoxy compound, compound 34d, is similarly prepared from the compound of the previous preparation.

EXAMPLE 1

4'-Benzyloxycarbonyl-4'-demethyl-4-O-(2,3-di-O-acetyl-4,6-O-ethylidene-β-D-altropyranosyl)epipodophyllotoxin (9a)

To a cooled and stirred solution of 4'-benzyloxycarbonyl-4'-demethylepipodophyllotoxin (8, 226 mg, 0.4 mmol) and 7a (232 mg, 0.8 mmol) in 20 ml of dry 1,2-dichloroethane was added 0.15 ml (1.2 mmol) of boron trifluoride etherate at −18° C. and the mixture was stirred at −18° C. for 45 min. To the mixture was added 0.3 ml of dry pyridine and the mixture was stirred at −18° C. for 10 min. The mixture was extracted with 100 ml of chloroform and the extract was washed with water, a saturated aqueous NaHCO$_3$ solution, water and brine successively and dried over MgSO$_4$. The dried extract was evaporated and the residue was chromatographed on a silica gel column (Kiesel gel 60, 30 g). The column was eluted with toluene-ethyl acetate (2:1). The desired fractions, by monitoring with TLC (Toluene-ethyl acetate=1:1), were collected and evaporated to dryness, which was triturated with ether to give 250 mg (75%) of the title compound 9a. MP 135°-140° C. IRνmax (KBr) cm$^{-1}$ 1767, 1600, 1507, 1486, 1234, 1218, 1165, 1132, 1099, 1072, 1038. UVλmax (MeOH) nm (ε) 292 (3000). Est'd purity 90% by HPLC; (75% MeOH-Buffer (pH 7)).

Anal: Calcd for C$_{43}$H$_{42}$O$_7$H$_2$O: C 60.84, H 5.22. Found: C 60.56, H 5.24.

EXAMPLE 2

4'Demethyl-4-O-(2,3-di-O-acetyl-4,6-O-ethylidene-β-D-altropyranosyl)epipodophyllotoxin (10a)

A mixture of 220 mg (0.265 mmol) of 9a and 100 mg of 10% palladium on carbon in 20 ml of ethanol and 20 ml of acetone was hydrogenated for 1.5 hours under one atmosphere pressure. The catalyst was removed by filtration, washed with acetone. The filtrate and washings were combined and evaporated to dryness. The residue was chromatographed on a silica gel column (Kiesel gel 60, 15 g). The column was eluted with toluene-ethyl acetate (1:1) and desired fractions by monitoring with TLC, were collected and evaporated to dryness. The residue was triturated with ether to give 155 mg (90%) of the title compound 10a. MP 205°–210° C. (dec.). IR$\nu_{max}$ (KBr) cm$^{-1}$ 3400, 1762, 1610, 1507, 1485, 1373, 1230, 1190, 1113, 1098, 1072, 1039. UV$\lambda_{max}$ (MeOH) nm ($\epsilon$) 235 (sh) (12,000), 285 (2,900). $^1$H NMR (CDCl$_3$) δ1.34 (3H, d, J=5.13 Hz, CH—CH$_3$), 2.11 (3H, s, OAc), 2.13 (3H, s, OAc), 4.79 (1H, q, J=5.13 Hz, CH—CH$_3$), 4.97 (1H, d, J=3.30 Hz, AG-H-4), 5.00 (1H, d, J=1.10 Hz, sugar-H-1), 5.02 (1H, dd, J=3.30 and 1.10 Hz, sugar-H-2), 5.29 (1H, t, J=3.30 Hz, sugar-H-3).

Anal: Calcd for C$_{33}$H$_{36}$O$_{15}$: C 58.93, H 5.40. Found: C 58.70, H 5.41.

Deacetylation of 10a; Preparation of 4'-Demethyl-4-O-(4,6-O-ethylidene-β-D-altropyranosyl)epipodphyllotoxin (11a), 4'-Demethyl-4-O-(3-O-acetyl-4,6-O-ethylidene-β-D-altropyranosyl)epipodophyllotoxin (12) and 4'-Demethyl-4-O-(2-O-acetyl-4,6-O-ethylidene-β-D-altropyranosyl)epipodophyllotoxin (13)

A mixture of 1.1 g (1.6 mmol) of 10a and 3.52 g (16 mmol) of zinc acetate dihydrate in 50 ml of ethanol and 50 ml of dioxane was refluxed for 16 hours with stirring and the mixture was evaporated to dryness. The residue was extracted with chloroform containing 1 ml of acetic acid and the extract was washed with an aqueous NaHCO$_3$ solution, water and brine and dried with MgSO$_4$. The extract was evaporated to dryness and the residue was chromatographed on a silica gel column (Kiesel gel 60, 50 g). The column was eluted with chloroform-methanol (100:1).

The first fractions were evaporated to dryness to give 142 mg (9%) of the starting material (10a). The second fractions were evaporated to dryness to give 334 mg (32%) of the 2-O-acetyl derivative (13). The third fractions were evaporated to dryness, which was purified by preparative HPLC to give 77 mg (8%) of the 3-O-acetyl derivative (12). The fourth fractions were collected and evaporated to dryness, which was triturated with ether to give 145 mg (15%) of the complete deacetylated compound (11).

Data of 11a

MP ca. 280° C. (grad. dec.) Est'd purity>95% by HPLC (55% MeOH-Buffer; retention time: 4.0 min). IR$\nu_{max}$ (KBr) cm$^{-1}$ 1767, 1730, 1610, 1518, 1507, 1486, 1231, 1164, 1111. UV$\lambda_{max}$ (MeOH) nm ($\epsilon$) 238 (sh) (12,000), 285 (4,000).

Anal: Calcd for C$_{29}$H$_{32}$O$_{13}$½H$_2$O: C 58.29, H 5.57. Found: C 58.50, H 5.57.

Data of 12

MP 160°–165° C. (dec.). Est'd purity 90% by HPLC (55% MeOH-Buffer pH 7; retention time: 7.7 min). IR$\nu_{max}$ (KBr) cm$^{-1}$ 3426, 1777, 1754, 1612, 1512, 1505, 1485, 1234, 1117, 1039. UV$\lambda_{max}$ (MeOH) nm ($\epsilon$) 238 (sh) (12,000), 286 (3,900).

Anal: Calcd for C$_{31}$H$_{34}$O$_{14}$½H$_2$O: C 58.21, H 5.52. Found: C 58.13, H 5.76.

Data of 13

MP 180°–190° C. (dec.). Est'd purity>95% by HPLC (55% MeOH-Buffer; retention time: 6.7 min). IR$\nu_{max}$ (KBr) cm$^{-1}$ 3470, 1777, 1754, 1613, 1513, 1505, 1484, 1230, 1160, 1090. UV$\lambda_{max}$ (MeOH) nm ($\epsilon$) 238 (sh) (12,000), 284 (3,900).

Anal: Calcd for C$_{31}$H$_{34}$O$_{14}$H$_2$O: C 57.40, H 5.59. Found: C 57.86, H 5.56.

EXAMPLE 3

4'-Benzyloxycarbonyl-4'-demethyl-4-O-(3-O-acetyl-2-deoxy-4,6-O-ethylidene-2-fluoro-β-D-altropyranosyl)epipodophyllotoxin (9b)

To a cooled and stirred solution of 4'-benzyloxycarbonyl-4'-demethylepipodophyllotoxin (8, 830 mg, 1.47 mmol) and 7b (550 mg, 2.2 mmol) in dry 1,2-dichloroethane (50 ml) was added boron trifluoride etherate (0.55 ml, 4.4 mmol) at −18° C. and the mixture was stirred at −18° C. for one hour. To the mixture was added 1 ml of pyridine and the mixture was stirred at −18° C. for 5 min. The mixture diluted with 100 ml of chloroform was washed with water, a saturated NaHCO$_3$ solution, water and brine successively, and dried over MgSO$_4$. The dried extract was concentrated to dryness and the residue was chromatographed on a silica gel column (Kiesel gel 60, 30 g). The column was eluted with toluene-ethyl acetate (4:1). The first fractions were collected and evaporated to dryness to give 27 mg (2.4%) of the α isomer of the title compound the structure of which was determined by NMR spectrum (400 MHz) as a minor product. The second fractions were collected and evaporated to dryness to give 959 mg (85%) of the desired compound (9b). MP ca. 145° C. (grad. dec.). Est'd purity: 80% HPLC (80% MeOH-pH 7 buffer). IR$\nu_{max}$ (KBr) cm$^{-1}$ 1772, 1600, 1507, 1486. UV$\lambda_{max}$ (MeOH) nm ($\epsilon$) 290.5 (3900).

Anal: Calcd for C$_{39}$H$_{39}$O$_{15}$F: C 61.09, H 5.13. Found: C 60.86, H 5.13.

Similarly the compounds (9c and 9d) were prepared by glycosidation of the alcohols (7c and 7d) with 8, respectively.

All of the corresponding 3-fluoro compounds are similarly prepared.

4'-Benzyloxycarbonyl-4'-demethyl-4-O-(3-O-acetyl-2-azido-2-deoxy-4,6-O-ethylidene-β-D-altropyranosyl)epipodophyllotoxin (9c)

MP 120°–130° C. Estimated purity: 85% by HPLC. IR$\nu_{max}$ (KBr) cm$^{-1}$ 2109, 1772, 1602, 1507, 1485. UV$\lambda_{max}$ (MeOH) nm ($\epsilon$) 291 (4100).

Anal: Calcd for C$_{39}$H$_{39}$N$_3$O$_{15}$: C 59.31, H 4.98, N 5.32. Found: C 59.28, H 5.02, N 5.33.

4'-Benzyloxycarbonyl-4'-demethyl-4-O-(3-O-acetyl-2-deoxy-β-D-altropyranosyl)epipodophyllotoxin (9d)

MP 150° C. Estimated purity: 80% by HPLC. IR$\nu_{max}$ (KBr) cm$^{-1}$ 1772, 1746, 1600, 1485. UV λmax(-MeOH) nm ($\epsilon$) 291 (2700).

Anal: Calcd for $C_{31}H_{40}O_{15} \cdot H_2O$: C 61.09, H 5.52. Found: C 61.25, H 5.31.

The corresponding 3-azido and 2-O-acetyl compounds are similarly prepared from the appropriate starting compounds.

EXAMPLE 4

4'-Demethyl-4-O-(3-O-acetyl-2-deoxy-4,6-O-ethylidene-2-fluoro-β-D-altropyranosyl)epipodophyllotoxin (10b)

A mixture of 9b (825 mg, 1.077 mmol) and 10% palladium on carbon (100 mg) in ethanol (50 ml) and acetone (50 ml) was hydrogenated for one hour under one atmospheric pressure. The catalyst was removed by filtration, and washed with methanol. The filtrate and washings were evaporated to dryness and the residue was chromatographed on a silica gel column (Kiesel gel 60, 60 g). The column was eluted with toluene-ethyl acetate (3:1–2:1). The desired fraction, by monitoring with TLC, was collected and evaporated to dryness to give 620 mg (91%) of the title compound (10b). MP 209°–212° C. IR$\nu$max (KBr) cm$^{-1}$ 1762, 1610, 1484. UV λmax(MeOH) nm ($\epsilon$) 235 (sh) (13,000), 284.5 (4,000).

Anal: Calcd for $C_{31}H_{38}O_{13}F$: C 58.86, H 5.26. Found: C 58.67, H 5.21.

Similar hydrogenolysis of 9c and 9d afforded the 4'-phenols, 10c, and 10d, respectively.

The corresponding 3-fluoro compounds are similarly prepared from the appropriate starting compounds.

4'-Demethyl-4-O-(3-O-acetyl-2-azido-2-deoxy-4,6-O-ethylidene-β-D-altropyranosyl)epipodophyllotoxin (10c)

MP 150°–160° C. Estimated purity: 95% by HPLC. IR$\nu$max (KBr) cm$^{-1}$ 3438, 2107, 1615, 1502. UV λmax (MeOH) nm ($\epsilon$) 238 (sh, 12,800), 285 (4,100).

Anal: Calcd for $C_{31}H_{33}N_3O_{13} \cdot \frac{1}{4}$ toluene: C 57.96, H 5.20, N 6.19. Found: C 57.67, H 5.21, N 6.08.

4'-Demethyl-4-O-(3-O-acetyl-2-deoxy-4,6-O-ethylidene-β-D-altropyranosyl)epipodophyllotoxin (10d)

MP 185°–188° C. Estimated purity: 95% by HPLC. IR$\nu$max (KBr) cm$^{-1}$ 1759, 1610, 1484, 1230, 1217. UV λmax (MeOH) nm ($\epsilon$) 237 (sh, 12,000), 285 (3,900).

Anal: Calcd for $C_{31}H_{34}O_{13}$: C 60.58, H 5.58. Found: C 60.58, H 5.60.

The corresponding 3-azido and 2-O-acetyl compounds are similarly prepared from appropriate starting compounds.

4'-Demethyl-4-O-(3-O-acetyl-2-amino-2-deoxy-4,6-O-ethylidene-β-D-altropyranosyl)epipodophyllotoxin hydrochloride (10e)

This compound was prepared by hydrogenation of 9c under different conditions (solvents, reaction period etc.) from those in reduction of 9c to 10c.

A mixture of 900 mg (1.1 mmol) of 9c and 500 mg of 10% palladium on carbon in a mixture of 40 ml of acetic acid and 8 ml of ethanol was hydrogenated at room temperature for 4 hours under one atmospheric pressure. The catalyst was removed by filtration, washed twice with 20 ml of methanol. The filtrate and washings were combined and the mixture was evaporated to dryness and the residue was chromatographed on a silica gel column (Kiesel gel 60, 20 g). The column was washed with chloroform and then, eluted with chloroform-methanol (25:1). The desired fractions by monitoring with TLC, were collected and evaporated to dryness and the residue was triturated with ether to give 452 mg (63%) of the title compounds (35) of free amine. MP 245°–250° C. (dec.); IR $\nu_{max}$ (KBr) cm$^{-1}$ 1770, 1740, 1600, 1480, 1230, 1110, 1040; UV $\lambda_{max}$ (MeOH) nm ($\epsilon$) 285 (4100), 292 (4000).

The free amine (308 mg, 0.5 mmol) was suspended in 5 ml of methanol. To the suspension was added 1 ml (2.7 mmol) of 10% hydrogen chloride in methanol to give a clear solution. The solution was diluted with 100 ml of ether and the resulting solid was collected by filtration, washed with ether to give 300 mg (92%) of the title compound (10e). MP ca. 215° C. (dec.); IR $\nu_{max}$ (KBr) cm$^{-1}$ 1750, 1610, 1480, 1230, 1100, 1030; UV $\lambda_{max}$ (MeOH) nm ($\epsilon$) 285 (3,500); Estimated purity 95% (by HPLC; 60% MeOH-Buffer; 4.7 min); MS FAB(+), m/z 630 (M+1)$^+$; $^1$H NMR (400 MHz, D$_2$O) δ5.42 (1H, d, J=1.83 Hz, H-1), 3.66 (1H, m, H-2), 5.50 (1H, t, J=2.93 Hz, H-3), 5.00 (1H, q, J=5.13 Hz, H-7), 1.36 (1H, d, J=5.13 Hz, H-8), 2.20 (3H, s, OAc).

EXAMPLE 5

4'-Demethyl-4-O-(2-deoxy-4,6-O-ethylidene-2-fluoro-β-D-altropyranosyl)epipodophyllotoxin (11b)

A mixture of 10b (520 mg, 0.8 mmol) and zinc acetate dihydrate (530 mg, 2.4 mmol) in methanol (100 ml) was refluxed for 16 hours with stirring and the mixture was evaporated to dryness. The residue was extracted with 100 ml of chloroform containing 0.4 ml of acetic acid and the extract was washed with water and brine, and dried over MgSO$_4$. After removal of the solvent, the residue chromatographed on a silica gel column. The column was eluted with chloroform-methanol (100:1) and the desired fractions, by monitoring with TLC, were collected and evaporated to dryness. The residue was triturated with ether to give 468 mg (79%) of 11b. MP 277°–279° C. (dec.). IR$\nu_{max}$(KBr) cm$^{-1}$ 1764, 1610, 1484. UVλ$_{max}$ (MeOH) nm ($\epsilon$) 235 (sh) (14,000), 284 (4,300).

Anal: Calcd for $C_{29}H_{31}O_{12}F$: C 58.98, H 5.29. Found: C 58.98, H 5.30.

Also deacetylation of 10c and 10d afforded 11c and 11d respectively.

The corresponding 3-fluoro compound is similarly prepared from the appropriate starting compounds.

4'-Demethyl-4-O-(2-azido-2-deoxy-4,6-O-ethylidene-β-D-altropyranosyl)epipodophyllotoxin (11c)

MP 283°–285° C. Estimated purity: 95% by HPLC. IR$\nu_{max}$(KBr) cm$^{-1}$ 3438, 2107, 1767, 1615, 1517. UVλ$_{max}$ (MeOH) nm ($\epsilon$) 238 (sh, 12,000), 286 (4,000).

Anal: Calcd for $C_{29}H_{31}N_3O_{12} \cdot Et_2O$: C 57.63, H 6.01, N 6.11. Found: C 57.21, H 5.89, M 6.08.

4'-Demethyl-4-O-(2-deoxy-4,6-O-ethylidene-β-D-altropyranosyl)epipodophyllotoxin (11d)

MP 288°–292° C. Estimated purity: 95% by HPLC. IR$\nu_{max}$ (KBr) cm$^{-1}$ 3300, 1762, 1610, 1484. UVλ$_{max}$ (MeOH) nm ($\epsilon$) 237 (sh, 12,000), 286 (4,000), 291 (3,900).

Anal: Calcd for $C_{29}H_{32}O_{12}$: C 60.83, H 5.63. Found: C 60.76, H 5.76.

EXAMPLE 6

4'-Demethyl-4-O-(2-amino-2-deoxy-4,6-O-ethylidene-β-D-altropyranosyl)epipodophyllotoxin (14)

A mixture of 11c (203 mg, 0.33 mmol) and 10% palladium on charcoal (200 mg) in acetic acid (15 ml) and ethanol (5 ml) was hydrogenated for 4 hours under one atmosphere pressure. The catalyst was removed by filtration and washed with 50 ml of methanol. The filtrate and washings were combined and evaporated to dryness. The residue was chromatographed on a silica gel column (Kiesel gel 60, 20 g). The column was eluted with chloroform-methanol (50:1–25:1). The desired fractions, by eluting with chloroform-methanol (25:1), were collected and evaporated to dryness, which was triturated with ether to give 98 mg (50.5%) of 14 as a free amine. MP 285°–288° C. (dec.). Estimated purity: 95% pure by HPLC. IR$\nu$max (KBr) cm$^{-1}$ 3380, 1765, 1610, 1461, 1230, 1137, 1089, 1034. UV λmax (MeOH) nm ($\epsilon$) 238 (sh, 13,000), 285 (4,200).

Anal: Calcd for $C_{29}H_{33}NO_{12}$: C 59.28, H 5.66, N 2.38. Found: C 59.10, H 5.87, N 2.24.

The free amine (60 mg, 0.1 mmol) was dissolved in 4 ml of dioxane and to the solution was added 0.1 ml (0.27 mmol) of 10% hydrogen chloride in methanol and the mixture was concentrated to 2 ml below 30° C. The concentrate was lyophilized to give 62 mg (100%) of the hydrochloride of 14. IR$\nu$max (KBr) cm$^{-1}$ 1770, 1610, 1507, 1458. UV λmax (MeOH) nm ($\epsilon$) 238 (11,000), 285 (3,700).

The corresponding 3-amino-3-deoxy compound is similarly prepared.

EXAMPLE 7

Disodium 4'-demethyl-4-O-(2-deoxy-4,6-O-ethylidene-2-fluoro-β-D-altropyranosyl)epipodophyllotoxin-4'-deoxy-4'-phosphate (15)

To a cooled and stirred solution of 11b (118 mg, 0.2 mmol) and N,N-diisopropylethylamine (0.52 ml, 3 mmol) in dry acetonitrile (10 ml) was added at 5° C. a solution of phosphorous oxychloride (122 mg, 0.8 mmol) in dry acetonitrile (0.5 ml) and the mixture was stirred at 5° C. for 10 minutes. To the reaction mixture was added 1 ml of water and concentrated to 2 ml below 30° C. The concentrate was dissolved in 10 ml of water containing 300 mg of NaHCO$_3$ and the solution was washed with 30 ml of ether. The aqueous layer was charged on a column packed with 50 ml of the packing of a prep PAK-C$_{18}$ cartridge (Waters). The column was washed with water and then eluted with 20% methanol and 30% methanol successively. The desired fractions eluted with 20% methanol were collected and concentrated to 5 ml and lyophilized to give 50 mg of 15. The crude fractions eluted with 20% methanol and 30% methanol were collected and concentrated to 10 ml and lyophilized to give 50 mg of crude product, which was repurified with preparative HPLC to give 17 mg of 15. The total yield of 15 was 67 mg (49%). MP 190°–195° C. (dec.). Estimated purity: >95% by HPLC. IR$\nu_{max}$ (KBr) cm$^{-1}$ 1772, 1600, 1506, 1486, 1235. UVλ$_{max}$ (MeOH) nm ($\epsilon$) 289.5 (3,500).

The corresponding 3-fluoro compound is similarly prepared.

The corresponding 3-azido compound and 2-deoxy epimer are similarly prepared from appropriate starting compounds.

EXAMPLE 8

O-Methylation of benzyl 4,6-O-ethylidene-α-D-altropyranoside (5a); Benzyl 2,3-di-O-methyl-4,6-O-ethylidene-α-D-altropyranoside (16), benzyl 4,6-O-ethylidene-2-O-methyl-α-D-altropyranoside (17) and benzyl 4,6-O-ethylidene-3-O-methyl-α-D-altropyranoside (18)

To a solution of 2.23 g (7.5 mmol) of benzyl 4,6-O-ethylidene-α-D-altropyranoside (5a in 15 ml of DMSO was added 360 mg (7.5 mmol) of 50% sodium hydroxide in an oil and the mixture was stirred at room temperature for 30 min. To the mixture was added 10 ml of methyl iodide and the mixture was stirred at room temperature for 30 min. The reaction mixture was extracted with 150 ml of chloroform, washed with water and brine successively, and dried over MgSO$_4$. The dried extract was evaporated to dryness and the oily residue was chromatographed on a silica gel column (Kiesel gel 60, 50 g). The column was eluted with toluene-ethyl acetate (5:1–2:1). The first fractions eluted with toluene-ethyl acetate (5:1) were collected and evaporated to dryness to give 920 mg (38%) of 16. $^1$H NMR (CDCL$_3$) δ3.40 and 3.55 (each 3H, s, OCH$_3$), 4.79 (1H, br-s, H-1).

The second fraction eluted with toluene-ethyl acetate (5:1) were collected and evaporated to dryness to give 250 mg (10%) of 17. $^1$H NMR (CDCl$_3$) δ3.42 (3H, s, OCH$_3$), 4.89 (1H, br-s, H-1).

The third fractions eluted with toluene-ethyl acetate (2:1) were collected and evaporated to dryness to give 780 mg (33.5%) of 18. $^1$H NMR (CDCl$_3$) δ3.55 (3H, s, OCH$_3$), 4.71 (1H, br-s, H-1).

The final fractions eluted with toluene-ethyl acetate (2:1) were collected and evaporated to dryness to give 400 mg (18%) of the starting material 5a.

EXAMPLE 9

2,3-Di-O-methyl-4,6-O-ethylidene-D-altropyranose (19)

A mixture of 920 mg (2.84 mmol) of 16 and 500 mg of 10% palladium on carbon in 10 ml of acetic acid and 2 ml of ethanol was hydrogenated at room temperature for 20 hours under one atmospheric pressure. The catalyst was removed by filtration, washed twice with 20 ml of methanol. The filtrate and washings were combined and the mixture was evaporated to dryness. The oily residue was chromatographed on a silica gel column (Kiesel gel 60, 30 g). The column was eluted with toluene-ethyl acetate (2:1). The desired fractions were collected by monitoring with TLC and evaporated to dryness to give 650 mg (98%) of the title compound 19 as an oil, consisting of a mixture of α and β anomers, which was shown by its NMR spectrum (400 MHz). $^1$H NMR (CDCl$_3$) δ 3.53 and 3.54 (each 3H, s, OCH$_3$ of α-anomor), 3.45 and 3.61 (each 3H, s, OCH$_3$ of β-anomer), 4.99 (1H, br-s, H-1α) 5.00 (1H, br-s, H-1 β).

EXAMPLE 10

3-O-Acetyl-4,6-O-ethylidene-2-O-methyl-D-altropyranose (20)

Acetic anhydride (2.5 ml) was added to a solution of 250 mg (0.8 mmol) of 17 and 25 mg of N,N-dimethylaminopyridine in 5 ml of dry pyridine and the mixture was stirred at room temperature for 30 min. To the mixture was added 5 ml of methanol and the solution was evaporated to dryness. The residue was extracted with 50 ml of ethyl acetate, washed with 2N sulfuric acid, water and brine, successively, and dried over MgSO$_4$. The extract was evaporated to dryness and the oily residue was chromatographed on a silica gel column (Kiesel gel 60, 15 g). The column was eluted with toluene-ethyl acetate (5:1) and the desired fractions were collected by monitoring with TLC, and evaporated to dryness to give 290 mg (>100%) of the 3-O-acetylated compound as an oil. $^1$H NMR (CDCl$_3$) δ2.03 (3H, s, OCOCH$_3$), 3.48 (3H, s, OCH$_3$), 4.84 (1H, br-s, H-1).

A mixture of 280 mg (0.795 mmol) of the 3-O-acetyl compound and 280 mg of 10% palladium on carbon in 5 ml of acetic acid and 1 ml of ethanol was hydrogenated at room temperature for 3 days under one atmospheric pressure. The catalyst was removed by filtration, washed twice with 10 ml of methanol. The filtrate and washings were combined and the solution was evaporated to dryness. The oily residue was chromatographed on a silica gel column (Kiesel gel 60, 20 g). The column was eluted with toluene-ethyl acetate (5:1-2:1). The desired fractions eluted with toluene-ethyl acetate (5:1-2:1). The desired fractions eluted with toluene-ethyl acetate (2:1) were collected and evaporated to dryness to give 160 mg (77%) of the title compound (20) as an oil. The $^1$H NMR (400 MHz) spectrum showed that the product consisted of a mixture of α and β anomers. $^1$H NMR (CDCl$_3$) δ4.95 (1H, d, J=1.3 Hz, H-1 H-1α), 5.09 (1H, br-s, H-1β), 5.33 (1H, t, J=3.3 Hz, H-3β), 5.47 (1H, t, 3.3 Hz, H-3α).

EXAMPLE 11

2-O-Acetyl-4,6-O-ethylidene-3-O-methyl-D-altropyranose (21)

The 2-O-acetyl derivative (21) was prepared by a similar procedure to that described in the preparation 3-O-acetyl derivatives (20). Thus O-acetylation of 18 (780 mg, 2.5 mmol) with acetic anhydride gave 860 mg (98%) of an intermediate benzyl 2-O-acetylaltropyranoside as an oil. $^1$H NMR (CDCl$_3$) δ2.09 (3H, s, OCOCH$_3$), 3.57 (3H, s, OCH$_3$), 4.71 (1H, br-s, H-1) 5.18 (dd, J=3.00 and 0.85 Hz, H-2).

The above 2-O-acetyl compound (850 mg, 2.4 mmol) was hydrogenated in the presence of 10% palladium on carbon (500 mg) in acetic acid and ethanol to give 580 mg (92%) of 21 as an oil, which consisted of a mixture of α- and β-anomers on NMR (400 MHz) spectrum. $^1$H NMR (CDCl$_3$) δ4.92 (1H, br-s, H-1α), 5.03 (1H, dd, J=3.9 and 1.3 Hz, H-2α), 5.16 (1H, br-s, H-1β), 5.04 (1H, dd, J=4.7 and 1.7 Hz, H-2β).

EXAMPLE 12

4'-Demethyl-4-O-(2,3-di-O-methyl-4,6-O-ethylidene-β-D-altropyranosyl)epipodophyllotoxin (22)

To a cooled and stirred solution of 320 mg (0.6 mmol) of 4'-demethyl-4'-benzyloxycarbonylepipodophyllotoxin (8) and 170 mg (0.726 mmol) of 19 in 20 ml of dry 1,2-dichloroethane was added at −18° C., 0.25 ml (2 mmol) of boron trifluoride etherate and the mixture was stirred at −18° C. for 30 min. To the mixture was added 0.25 ml of pyridine and the mixture was stirred at the same temperature for 5 min. The mixture was extracted with 100 ml of chloroform, washed with aqueous NaHCO$_3$, water and brine, successively, and dried over MgSO$_4$. After removal of the solvent, the residue was chromatographed on a silica gel column (Kiesel gel 60, 20 g). The column was eluted with toluene-ethyl acetate (3:1) and the desired fractions were collected by monitoring with TLC and evaporated to dryness, which was triturated with ether-n-hexane to give 145 mg (32%) of the 4'-O-benzyloxycarbonyl derivative of 22. MP 125°-132° C. (dec.). IRν$_{max}$ (KBr) cm$^{-1}$ 1772, 1602, 1484, 1235, 1109, 1044. UVλ$_{max}$ (MeOH) nm (ε) 292 (4700). $^1$H NMR (CDCl$_3$) δ3.49 and 3.51 (each 3H, s, OCH$_3$), 4.94 (1H, d, J=0.36 Hz, H-1").

A mixture of 135 mg (0.18 mmol) of the above O-benzyloxycarbonyl derivative and 50 mg of 10% palladium on carbon in 10 ml of ethanol and 10 ml of acetone was hydrogenated at room temperature for 5 minutes under one atmospheric pressure. The catalyst was removed by filtration, washed twice with 10 ml of acetone. The filtrate and washings were combined and the solution was evaporated to dryness. The residue was chromatographed on a silica gel column (Kiesel gel 60, 15 g). The column was eluted with toluene-ethyl acetate (2:1). The desired fractions were collected by monitoring with TLC (toluene:ethyl acetate=1:1) and evaporated to dryness. The residue was triturated with ether to give 76 mg (68.5%) of the title compound 22. MP 140°-150° C. (dec.). IRν$_{max}$ (KBr) cm$^{-1}$ 1774, 1751, 1616, 1485, 1230, 1111, 1040. UVλ$_{max}$ (MeOH) nm (ε) 237 (sh, 10,000), 284 (3,300). $^1$H NMR (CDCl$_3$) δ4.94 (1H, d, J=0.85 Hz, H-1"), 3.37 (1H, dd, J=3.42 and 0.85 Hz, H-2"), 4.71 (1H, q, J=5.13 Hz, H-7"), 1.37 (3H, d, J=5.13, H-8"), 3.49 and 3.50 (each 3H, s, OCH$_3$).

Anal: Calcd for C$_{31}$H$_{36}$O$_{13}$·2.5H$_2$O: C 56.23, H 6.25. Found: C 56.39, H 6.61.

EXAMPLE 13

4'-Demethyl-4-O-(4,6-O-ethylidene-2-O-methyl-β-D-altropyranosyl)epipodophyllotoxin (23)

Glycosidation of 8 with 20 followed by debenzyloxycarbonylation was carried out by a similar procedure to that described in the preparation of 22. Thus glycosidation of 8 with 20 (150 mg, 0.57 mmol) gave 230 mg (59%) of the glycosylated product as powder. MP 132°-134° C. (dec.). IRν$_{max}$ (KBr) cm$^{-1}$ 1772, 1602, 1485, 1235, 1109, 1040. UVλ$_{max}$ (MeOH) nm (ε) 291 (4,300). $^1$H NMR (CDCl$_3$) δ4.91 (1H, d, J=0.85 Hz, H-1"), 3.35 (1H, dd, J=3.84 and 1.28 Hz, H-2"), 5.34 (1H, dd, J=3.42 and 2.66 Hz, H-3"), 4.76 (1H, q, J=5.13 Hz, H-7"), 1.34 (3H, d, J=5.13 Hz, H-8") 3.51 (3H, s, OCH$_3$), 2.12 (3H, s, OAc).

The above glycosylated product (220 mg, 0.8 mmol) was hydrogenated in the presence of 10% palladium of carbon to give 210 mg (ca. 100%) of the 3"-O-acetyl derivative of 23. MP 140°-150° C. (dec.). IRν$_{max}$ (KBr) cm$^{-1}$ 1779, 1751, 1617, 1486, 1232, 1110, 1037. UVλ$_{max}$ (MeOH) nm (ε) 237 (sh, 13,000), 284 (3,900). $^1$H NMR (CDCl$_3$) δ4.91 (1H, d, J=0.86 Hz, H-1"), 3.35 (1H, dd, J=3.42 and 0.86 Hz, H-2"), 5.34 (1H, t, J=3.42 Hz, H-3"), 4.75 (1H, q, J=5.13 Hz, H-7"), 1.34 (3H, d, J=5.13 Hz, H-8"), 3.51 (3H, s, OMe), 2.12 (3H, s, OAc).

A mixture of 200 mg (0.3 mmol) of the above 3"-O-acetyl compound and 660 mg (3 mmol) of zinc acetate dihydrate in 30 ml of dry methanol was refluxed for 6 hours with stirring and the mixture was evaporated to dryness. The residue was extracted with 100 ml of chloroform containing 0.5 ml of acetic acid, washed with water and brine and dried over MgSO$_4$. The dried extract was evaporated to dryness and the residue was chromatographed on a silica gel column (Kiesel gel 60, 20 g). The column was eluted with chloroform-methanol (100:1). The desired fractions were collected and evaporated to dryness, which was triturated with ether to give 94 mg (52%) of the title compound 23. MP 173°–180° C. (dec.). IR$\nu_{max}$ (KBr) cm$^{-1}$ 3445, 1772, 1615, 1518, 1507, 1485, 1286, 1190, 1116, 1037. UV $\lambda$max (MeOH) nm ($\epsilon$) 237 (sh, 12,000), 284 (3,800). $^1$H NMR (CDCl$_3$) δ5.03 (1H, d, J=1.10 Hz, H-1''), 3.89 (1H, dd, J=3.66 and 1.10 Hz, H-2''), 4.16 (1H, t, J=3.30 Hz, H-3''), 4.82 (1H, q, J=5.13 Hz, H-7''), 1.36 (3H, d, J=5.13 Hz, H-8''). 3.50 (3H, s, OCH$_3$).

Anal: Calcd for C$_{30}$H$_{34}$O$_{13}$. (C$_2$H$_5$)$_2$O: C 60.35, H 6.55. Found: C 60.33, H 6.60.

4'-Demethyl-4-O-(4,6-O-ethylidene-3-O-methyl-β-D-altropyranosyl)-epipodophyllotoxin (24)

According to the aforementioned procedures, glycosidation of 8 with 21 followed by hydrogenolysis and deacetylation was carried out to give the final compound 24.

(1) In the present glycosidation, both α- and β-glycoside products were able to be separately isolated. Thus, glycosidation of 8 (801 mg, 1.5 mmol) with 21 (530 mg, 2 mmol) gave a crude mixture of the α- and β-anomers, which was separated by a silica gel column chromatography (toluene:ethyl acetate=3:1) to give 400 mg (34%) of the β-D-altropyranosyl derivative and 570 mg (49%) of its α-anomer. These spectral data are as follows:

Glycosidation product (β-anomer)

MP 130°–135° C. (dec.). IR$\nu_{max}$ (KBr) cm$^{-1}$ 1772, 1602, 1485, 1235, 1108, 1042. UV$\lambda_{max}$ (MeOH) nm ($\epsilon$) 291 (4,100). $^1$H NMR (CDCl$_3$) δ5.03 (1H, d, J=1.28 Hz, H-1''), 5.05 (1H, dd, J=3.42 and 1.28 Hz, H-2'').

Glycosidation product (α-anomer)

MP 130°–135° C. (dec.). IR$\nu_{max}$ (KBr) cm$^{-1}$ 1772, 1742, 1602, 1484, 1235, 1106, 1039. UV$\lambda_{max}$ (MeOH) nm ($\epsilon$) 291 (4,200). $^1$H NMR (CDCl$_3$) δ4.80 (1H, br-s, H-1''), 5.07 (1H, d, J=2.56 Hz, H-2''), 3.61 (1H, t, J=2.93 Hz, H-3'').

(2) The above β-anomer (345 mg, 0.44 mmol) in acetone-ethanol was hydrogenated at one atmospheric pressure in the presence of 10% palladium on carbon to give 280 mg (98%) of the 2''-O-acetyl-4'-hydroxy derivative as colorless powder.

The 2''-O-acetyl-4'-hydroxy derivative

MP ca. 150° C. (dec.). IR$\nu_{max}$ (KBr) cm$^{-1}$ 1779, 1751, 1617, 1486, 1229, 1111, 1039. UV$\lambda_{max}$(MeOH) nm ($\epsilon$) 237 (sh, 13,000), 285 (3,900). $^1$H NMR (CDCl$_3$) δ5.03 (1H, d, J=1.46 Hz, H-1''), 5.05 (1H, dd, J=3.30 and 1.46 Hz, H-2''), 3.64 (1H, t, J=3.66 Hz, H-3'').

(3) Deacetylation of the above 2''-O-acetyl derivative (270 mg, 0.42 mmol) with zinc acetate dihydrate gave 163 mg (59%) of 24 as colorless powder.

Compound 24

MP 205°–210° C. (dec.). IR$\nu$max (KBr) cm$^{-1}$ 3475, 1772, 1751, 1617, 1485, 1232, 1193, 1162, 1110, 1039. UV $\lambda$max (MeOH) nm ($\epsilon$) 240 (11,000), 286 (3,500). $^1$H NMR (CDCl$_3$) δ5.00 (1H, d, J=1.10 Hz, H-1''), 3.86 (1H, dd, J=3.66 and 1.10 Hz, H-2''), 3.74 (1H, t, J=3.30 Hz, H-3''), 4.73 (1H, q, J=4.76 Hz, H-7''), 1.38 (3H, d, J=4.76 Hz, H-8''), 3.53 (3H, s, OMe).

Anal: Calcd for C$_{30}$H$_{34}$O$_{13}$: C 59.80, H 5.68. Found: C 59.70, H 5.82.

EXAMPLE 14

3-Azido-2,3-dideoxy-4,6-O-ethylidene-2-fluoro-α-D-altropyranose (27)

To a solution of benzyl-3-azido-4,6-O-benzylidene-2,3-dideoxy-2-fluoro-α-D-altropyranoside (420 mg, 1.09 mmol) in ethanol-water (4:1, 5 ml) was added p-toluenesulfonic acid (10 mg, 0.05 mmol) and the mixture was refluxed for 5 hr. The reaction mixture was concentrated, diluted with dichloromethane, washed with water, and dried over NaSO$_4$. The organic layer was concentrated to give 380 mg of crude solid, which was purified by silica gel column chromatography (Hexane:EtOAc=1:1) to obtain 274 mg (85%) of benzyl 3-azido-2,3-dideoxy-2-fluoro-α-D-altropyranoside. To a stirred solution of the above diol (274 mg, 0.92 mmol) in dichloromethane (4 ml) were added acetaldehyde dimethyl acetal (0.3 ml) and p-toluenesulfonic acid (10 mg) and the mixture was stirred at room temperature for 6 hr. The reaction mixture was quenched with aq. NaHCO$_3$, then washed with water, and dried over NaSO$_4$. The organic layer was concentrated to give 289 mg of colorless oil, which was purified by silica gel column (Hexane:EtOAc=2:1) to obtain 250 mg (84%) of the 4,6-O-ethylidene derivative.

To a solution of 4,6-O-ethylidene derivative (250 mg, 0.77 mmol) in CCl$_4$ (8 ml) was added NBS (243 mg) and the mixture was refluxed for 1 hr, and concentrated. To this residue diluted with acetone-water (4:1, 5 ml) was added Hg(CN)$_2$, and the mixture was stirred at room temperature for 4 hr. After a standard workup, the crude product obtained was chromatographed on a silica gel column to give 118 mg of the title compound (27) as a pure oil. $^1$H NMR (CDCl$_3$) δ5.40–4.56 (2H, m), 4.56–3.23 (7H, m), 1.37 (3H, d, J=5 Hz).

EXAMPLE 15

4'-Benzyloxycarbonyl-4'-demethyl-4-O-(3-azido-2,3-dideoxy-4,6-O-ethylidene-2-fluoro-β-D-altropyranosyl)epipodophyllotoxin (28)

To a solution of 4'-benzyloxycarbonyl-4'-demethylepipodophyllotoxin (8, 220 mg, 0.41 mmol) and 27 (118 mg, 0.53 mmol) in dichloroethane (6 ml) was added BF$_3$.Et$_2$O (104 μl) at −10° C. and the mixture was stirred at −10°−−5° C. for 1 hr. Then the reaction mixture was mixed with triethylamine (0.1 ml) and stirred at room temperature for 1 hr. After a standard workup, the crude product obtained was chromatographed on a silica gel column to give 227 mg (75%) of 28 as colorless powder. IR$\nu$max (KBr) cm$^{-1}$ 2114, 1771, 1602. UV $\lambda$max (MeOH) nm ($\epsilon$) 292 (3,140).

Anal: Calcd for C$_{37}$H$_{36}$N$_3$O$_{13}$F.3H$_2$O: C 55.29, H 5.27, N 5.23. Found: C 55.33, H 4.53, N 5.25.

EXAMPLE 16

4'-Demethyl-4-O-(3-azido-2,3-dideoxy-4,6-O-ethylidene-2-fluoro-β-D-altropyranosyl)epipodophyllotoxin (29)

A stirring solution of 28 (87 mg, 0.12 mmol) in ethanol-ethylacetate (4:1, 5 ml) was hydrogenated for 20 min in the presence of 10% Pd-C at 1 atm, and the catalyst was filtered off. The filtrate was concentrated to give the crude solid (75 mg), which was purified by a silica gel column to obtain 53 mg (73%) of 29 as colorless powder. MP 132°–134° C. Estimated purity 80% by HPLC (SSC-ODS-262, 65% MeOH-pH 7 buffer). IR$\nu$- max (KBr) cm$^{-1}$ 2120, 1777, 1616. UV λmax (MeOH) nm (ε) 240 (sh, 11,960), 285 (3,850). $^1$H NMR (CDCl$_3$) δ4.90 (1H, d, J=20.6 Hz, 1"-H), 4.80 (1H, q, J=4.8 Hz, 7"-H), 4.44 (1H, dd, J=4 and 47 Hz, 2"-H), 3.65 (1H, t, J=10 Hz, 6"ax-H), 1.40 (3H, d, J=4.8 Hz, 8"-CH3).

Anal: Calcd for C$_{29}$H$_{30}$N$_3$O$_{11}$F.½H$_2$O: C 55.77, H 5.00, N 6.73. Found: C 55.55, H 5.09, N 6.25.

EXAMPLE 17

4'-Demethyl-4-O-(3-amino-2,3-dideoxy-4,6-O-ethylidene-2-fluoro-β-D-altropyranosyl)epipodophyllotoxin (30)

A shaking suspension of 28 (100 mg, 0.14 mmol) in acetic acid-water (1:1, 10 ml) was hydrogenated overnight in the presence of PtO$_2$ (50 mg) at 55 psi. The catalyst was filtered off, and the filtrate was concentrated to give 120 mg of crude pale yellow oil, which was purified by a silica gel column to obtain 61 mg (77%) of 30 as colorless powder. MP 169°-172° C. Estimated purity 80% (by HPLC). IRνmax (KBr) cm$^{-1}$ 1775, 1610. UV λmax (MeOH) nm (ε) 237 (sh, 12,050), 285 (3,700). $^1$H NMR (DMSO-d$_6$) δ5.34 (1H, d, J=22.2 Hz, 1"-H), 4.85 (1H, q, J=5.1 Hz, 7"-H), 4.43 (1H, dd, J=3.5 and 47 Hz, 2"-H), 4.10 (1H, dd, J=5.1 and 10.3 Hz, 6"eq-H), 3.93 (1H, dt, J=5 and 10 Hz, 5"-H), 3.66 (1H, m, 4"-H), 3.56 (1H, t, J=10.3 Hz, 6"ax-H), 3.51 (1H, m, 3"-H), 1.24 (3H, d, J=5.1 Hz, 8"-CH3).

Anal: Calcd for C$_{29}$H$_{32}$NO$_{11}$F.3H$_2$O: C 54.12, H 5.95, N 2.18. Found: C 54.32, H 5.21, N 2.24.

EXAMPLE 18

Capsule Dosage Form

The following materials are blended in the dry state and then loaded into hard gelatin capsules to a fill weight of 0.345 g.
100 g 4'-Demethyl-4-O-(3-O-acetyl-2-deoxy-4,6-O-ethylidene-2-fluoro-β-D-altropyranosyl)epipodophyllotoxin.
2.0 g Magnesium stearate
30.0 g Microcrystalline cellulose (Avicel PH 102)
10.5 g Starch The batch is sufficient for 1000 capsules suitable for oral administration.

EXAMPLE 19

Suppository Dosage Form

A batch of 100 suppositories suitable for rectal administration is prepared from the following ingredients.
154.8 g of a hard friable low hydroxyl fat suppository base such as Witepsol H-15 (Dynamit-Nobel)
12 g of 4'-Demethyl-4-O-(4,6-O-ethylidene)-β-D-altropyranosyl)epipodophyllotoxin.

The fatty base material is melted at 50°-60° C. and then cooled to just above its melting point (35° C.) with moderate stirring. The active compound is then scattered on the surface of the melted base until the entire amount has been distributed during a 15 minute interval. Stirring is continued for one hour and then the blend is poured into preheated suppository molds. The mold and contents are then allowed to cool to 22°-26° C. and the suppositories are removed and packaged. Each suppository contains a dose equivalent to 100 mg of the antitumor agent.

EXAMPLE 20

Composition For Oral Administration

The following ingredients are mixed to provide liquid compositions for oral administration containing 100 mg of active compound per 5 ml of composition.
100 mg 4'-Demethyl-4-O-(3-O-acetyl-4,6-O-ethylidene-β-D-altropyranosyl)epipodophyllotoxin.
10 mg anhydrous citric acid
150 mg benzyl alcohol
400 mg polysorbate 80, purified
3.25 g polyethylene glycol 300
5.12 g absolute alcohol

EXAMPLE 21

Parenteral Composition

The composition of Example 18 is diluted 20 to 50 times with 0.9% sodium chloride or 5% dextrose for injection followed by slow intravenous infusion.

We claim:

1. A compound having the formula:

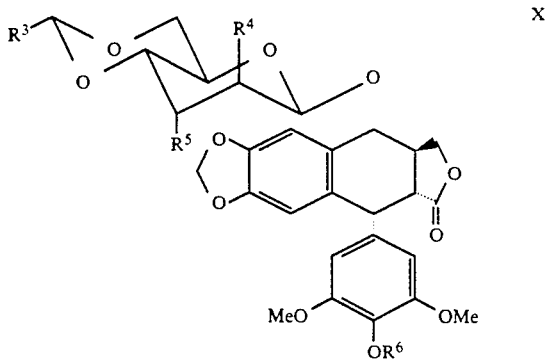

wherein R$^3$ is selected from the group consisting of (C$_1$-C$_{10}$) alkyl, phenyl, furyl and 2-thienyl;
wherein one of R$^4$ and R$^5$ is selected from the group consisting of hydroxy, C$_{1-5}$alkoxy and C$_{1-5}$acyloxy; and the other is selected from the group consisting of H, hydroxy, C$_{1-5}$alkoxy, C$_{1-5}$acyloxy, F, azido, and amino; or one of R$^4$ and R$^5$ is F and the other is selected from the group consisting of azido and amino; and R$^6$ is selected from the group consisting of hydrogen, P(O) (OH)$_2$ and alkali or alkaline earth metal salts thereof.

2. The compound of claim 1 which is 4'-demethyl-4-O-(3-O-acetyl-2-deoxy-4,6-O-ethylidene-2-fluoro-β-D-altropyranosyl)epipodophyllotoxin.

3. The compound of claim 1 which is 4'-demethyl-4-O-(4,6-O-ethylidene-β-D-altropyranosyl)epipodophyllotoxin.

4. The compound of claim 1 which is 4'-demethyl-4-O-(3-O-acetyl-4,6-O-ethylidene-β-D-altropyranosyl)epipodophyllotoxin.

5. The compound of claim 1 which is 4'-demethyl-4-O-(2-amino-2-deoxy-4,6-O-ethyliene-β-D-altropyranosyl)epipodophyllotoxin.

6. The compound of claim 1 which is 4'-demethyl-4-O-(2-deoxy-4,6-O-ethylidene-2-fluoro-β-D-altropyranosyl)epipodophyllotoxin.

7. The compound of claim 1 which is 4'-demethyl-4-O-(2,3-di-O-acetyl-4,6-O-ethylidene-β-D-altropyranosyl)epipodophyllotoxin.

8. The compound of claim 1 which is 4'-demethyl-4-O-(3-O-acetyl-2-azido-2-deoxy-4,6-O-ethylidene-β-D-altropyranosyl)epipodophyllotoxin.

9. The compound of claim 1 which is 4'-demethyl-4-O-(3-O-acetyl-2-deoxy-4,6-O-ethylidene-β-D-altropyranosyl)epipodophyllotoxin.

10. The compound of claim 1 which is 4'-demethyl-4-O-(2-azido-2-deoxy-4,6-O-ethylidene-β-D-altropyranosyl)epipodophyllotoxin.

11. The compound of claim 1 which is 4'-demethyl-4-O-(2-deoxy-4,6-O-ethylidene-β-D-altropyranosyl)epipodophyllotoxin.

12. The compound of claim 1 which is 4'-demethyl-4-O-(4,6-O-ethylidene-3-O-methyl-β-D-altropyranosyl)epipodophyllotoxin.

13. The compound of claim 1 which is 4'-demethyl-4-O-(3-O-acetyl-2-amino-2-deoxy-4,6-O-ethylidene-β-D-altropyranosyl)epipodophyllotoxin.

14. The compound of claim 1 which is 4'-demethyl-4-O-(2-O-acetyl-4,6-O-ethylidene-β-D-altropyranosyl)epipodophyllotoxin.

15. The compound of claim 1 which is 4'-demethyl-4-O-(4,6-O-ethylidene-2-O-methyl-β-D-altropyranosyl)epipodophyllotoxin.

16. The compound of claim 1 which is 4'-demethyl-4-O-(2,3-di-O-methyl-4,6-O-ethylidene-β-D-altropyranosyl)epipodophyllotoxin.

17. The compound of claim 1 which is disodium 4'-demethyl-4-O-(2-deoxy-4,6-O-ethylidene-2-fluoro-β-D-altropyranosyl)epipodophyllotoxin-4'-deoxy-4'-phosphate.

18. 4'-Benzyloxycarbonyl-4'-demethyl-4-O-(3-azido-2-fluoro-2,3-dideoxy-4,6-O-ethylidene-β-D-altropyranosyl)epipodophyllotoxin.

19. The compound of claim 1 which is 4'-demethyl-4-O-(3-azido-2,3-dideoxy-4,6-O-ethylidene-2-fluoro-β-D-altropyranosyl)epipodophyllotoxin.

20. The compound of claim 1 which is 4'-demethyl-4-O-(3-amino-2,3-dideoxy-4,6-O-ethylidene-2-fluoro-β-D-altropyranosyl)epipodophyllotoxin.

21. A pharmaceutical composition comprising an antitumor effective amount of a compound of claim 1 and a pharmaceutically acceptable carrier.

* * * * *